(12) United States Patent
Lim

(10) Patent No.: US 7,776,309 B2
(45) Date of Patent: Aug. 17, 2010

(54) PREPARATION AND USE OF ALKYLATING AGENTS

(75) Inventor: John L. Lim, Aiea, HI (US)

(73) Assignee: The Queen's Medical Center, Honolulu, HI (US)

( * ) Notice: Subject to any disclaimer, the term of this patent is extended or adjusted under 35 U.S.C. 154(b) by 0 days.

(21) Appl. No.: 10/900,066

(22) Filed: Jul. 26, 2004

(65) Prior Publication Data

US 2005/0123475 A1 Jun. 9, 2005

Related U.S. Application Data

(60) Provisional application No. 60/490,233, filed on Jul. 24, 2003.

(51) Int. Cl.
*A61K 51/00* (2006.01)
(52) U.S. Cl. .................. 424/1.11; 546/16; 546/44; 546/134; 546/276.4; 570/142
(58) Field of Classification Search .................. 570/142; 424/1.11; 546/16, 44, 134, 276.4
See application file for complete search history.

(56) References Cited

U.S. PATENT DOCUMENTS

| | | | |
|---|---|---|---|
| H74 H | 6/1986 | Shiue et al. | |
| 4,775,759 A | 10/1988 | Rice et al. | |
| 4,871,527 A | 10/1989 | Shiue et al. | |
| 4,885,464 A | 12/1989 | Stewart et al. | |
| 5,098,996 A | 3/1992 | Jacobson et al. | |
| 5,169,942 A | 12/1992 | Johnson et al. | |
| 5,219,548 A | 6/1993 | Yang et al. | |
| H1209 H | 7/1993 | Shiue et al. | |
| 5,545,397 A | 8/1996 | Spielvogel et al. | |
| 5,808,146 A | 9/1998 | Goodman et al. | |
| 5,817,776 A | 10/1998 | Goodman et al. | |
| 5,879,657 A | 3/1999 | DeGrado et al. | |
| 5,886,190 A | 3/1999 | Wallace et al. | |
| 6,019,957 A | 2/2000 | Miller et al. | |
| 6,022,523 A | 2/2000 | DeGrado et al. | |
| 6,187,284 B1 | 2/2001 | Griffiths | |
| 6,241,964 B1 | 6/2001 | Burns et al. | |
| 6,277,982 B1 | 8/2001 | Fraser et al. | |
| 6,278,020 B1 | 8/2001 | Patel et al. | |
| 6,281,380 B1 | 8/2001 | Prakash et al. | |
| 6,281,399 B1 | 8/2001 | Schulz et al. | |
| 6,281,405 B1 | 8/2001 | Davis et al. | |
| 6,288,233 B1 | 9/2001 | Kuo et al. | |
| 6,291,716 B1 | 9/2001 | Jun et al. | |
| 6,291,724 B1 | 9/2001 | Braat | |
| 6,294,499 B1 | 9/2001 | Watson et al. | |
| 6,303,840 B1 | 10/2001 | Poliakoff et al. | |
| 6,307,048 B1 | 10/2001 | Kuo et al. | |
| 6,313,362 B1 | 11/2001 | Green et al. | |
| 6,315,964 B1 | 11/2001 | Knifton et al. | |
| 6,339,179 B1 | 1/2002 | Schulz et al. | |
| 6,355,839 B1 | 3/2002 | Onopchenko | |
| 6,358,489 B1 | 3/2002 | Griffiths | |
| 6,362,352 B1 | 3/2002 | DeGrado et al. | |
| 6,376,729 B1 | 4/2002 | Merrill et al. | |
| 6,376,730 B1 | 4/2002 | Jan et al. | |
| 6,387,705 B1 | 5/2002 | Claibourn et al. | |
| 6,388,157 B1 | 5/2002 | Jan et al. | |
| 6,392,114 B1 | 5/2002 | Shields et al. | |
| 6,395,871 B1 | 5/2002 | Watson et al. | |
| 6,395,945 B1 | 5/2002 | Randolph | |
| 6,423,871 B1 | 7/2002 | Jung | |
| 6,429,349 B1 | 8/2002 | Grimes et al. | |
| 6,440,886 B1 | 8/2002 | Gajda et al. | |
| 6,448,458 B1 | 9/2002 | Marinangeli et al. | |
| 6,479,721 B1 | 11/2002 | Gajda et al. | |
| 6,486,374 B1 | 11/2002 | Radcliffe et al. | |
| 6,492,571 B1 | 12/2002 | He et al. | |
| 6,500,998 B1 | 12/2002 | Jan et al. | |
| 6,504,071 B2 | 1/2003 | Zhang et al. | |
| 6,512,153 B1 | 1/2003 | Cappellazzo et al. | |
| 6,515,169 B1 | 2/2003 | Marinangeli et al. | |
| 6,525,234 B1 | 2/2003 | Dandekar et al. | |
| 6,528,316 B1 | 3/2003 | Gosling | |
| 6,541,655 B2 | 4/2003 | Trost et al. | |
| 6,548,113 B1 | 4/2003 | Bimbaum et al. | |
| 6,552,241 B1 | 4/2003 | Randolph et al. | |
| 6,555,722 B2 | 4/2003 | Chen | |
| 6,567,492 B2 | 5/2003 | Kiselev et al. | |

(Continued)

FOREIGN PATENT DOCUMENTS

JP 9-48747 2/1997

(Continued)

OTHER PUBLICATIONS

Block et al. "The N.C.A. Nucleophilic 18F-Fluorination of 1,N-Disubstituted Alkanes as Fluoroalkylation Agents" Journal of Labelled Compounds and Radiopharmaceuticals 1987, vol. 24, pp. 1029-1042.*

(Continued)

*Primary Examiner*—Joseph R Kosack
(74) *Attorney, Agent, or Firm*—Morgan Lewis & Bockius LLP

(57) ABSTRACT

Methods of alkylating target compounds are disclosed. The alkylating agent can be radiolabelled. In some instances, the alkylating agent is synthesized and then reacted with a target compound without an intervening purification step. The method comprises a) synthesizing an alkylating agent having the formula:

$X—(CR^1R^2)_a CR^3R^4\text{-LG}$ wherein,
a is 0, 1, 2 or 3,
$R^1$, $R^2$, $R^3$ and $R^4$ are independently H, X or alkyl,
X is a halogen or a label, with the proviso that at least one X is a halogen,
LG is a leaving group; and b) directly reacting said alkylating agent with a target compound comprising an alkylation reactive group under conditions suitable for the alkylation of said target compound.

23 Claims, 10 Drawing Sheets

U.S. PATENT DOCUMENTS

| | | | |
|---|---|---|---|
| 6,583,953 | B1 | 6/2003 | Han et al. |
| 6,630,125 | B2 | 10/2003 | DeGrado et al. |
| 6,642,425 | B2 | 11/2003 | Winder et al. |
| 6,642,426 | B1 | 11/2003 | Johnson et al. |
| 6,664,432 | B2 | 12/2003 | Ackerman et al. |
| 6,673,977 | B2 | 1/2004 | Mauleon et al. |
| 6,677,269 | B2 | 1/2004 | Olah |
| 6,709,638 | B2 | 3/2004 | Randolph et al. |
| 6,747,152 | B2 | 6/2004 | Trost et al. |
| 6,750,354 | B2 | 6/2004 | Rauchschwalbe et al. |
| 6,759,349 | B2 | 7/2004 | Lewis et al. |
| 2002/0061279 | A1 | 5/2002 | DeGrado et al. |

FOREIGN PATENT DOCUMENTS

| | | |
|---|---|---|
| WO | WO 01/82864 A2 | 11/2001 |

OTHER PUBLICATIONS

McMurry, John "Organic Chemistry—Fourth Edition" Brooks/Cole Publishing Company, 1996, pp. 377-385.*

Zhao et al. "Mechanism, Structure-Activity Studies, and Potential Applications of Gluthathione S-Transferase-Catalyzed Clevage of Sulfonamides" Drug Metabolism and Disposition, 1999, vol. 27, No. 9, pp. 992-998.*

Anon., "[$^{18}$F]Chemical Process Control Unit," CTI, Inc.: Knoxville, TN (1996).

Block, et al., *J. Label. Compds. Radiopharm.* 24:1029-1042 (1987).

DeGrado, T., et al., "Synthesis and evaluation of $^{18}$F-labeled choline analogs as oncologic PET tracers," *J. Nucl. Med.* 42(12):1805-1814 (Dec. 2001).

DeGrado, T., et al., "Synthesis and evaluation of 18F-labeled choline as an oncologic tracer for positron emission tomography: initial findings in prostate cancer," *Cancer Res.* 61:110-117 (Jan. 2000).

DeJong, I., et al., "Imaging of bladder cancer using $^{11}$C choline," *J. Nucl. Med.* 41(5 Suppl.):74P (May 2000).

DeJong, I., et al., "Positron emission tomography: technique and application in urological oncology," *Nederlands. Tijdschrift voor Urologie* 7(2):44-50 (1999).

DeJong, I., et al., "Visualisation of bladder cancer using $^{11}$C-choline PET: first clinical experience," *Eur. J. Nucl. Med. Mol. Imag.* 29(10):1283-1288 (2002).

DeJong, I., et al., "Visualisation of prostate cancer with $^{11}$C-choline positron emission tomography," *Eur. Urol.* 42(1):18-23 (Jul. 2002).

Delbeke, D., "Oncological application of FDG PET imaging: brain tumors, colorectal cancer, lymphoma and melanoma," *J. Nucl. Med.* 40(4):591-603 (Apr. 1999).

Eskola, O., et al., "Synthesis of $^{18}$F-bromofluoromethane [$^{18}$F]FCH$_2$Br; fluoromethylation reagent with high specific radioactivity," *J. Labelled Cpd. Radiopharm.* 42(Supp. 1):S543-S545 (1999).

Friedland, R., et al., "Labeled choline and phosphorylcholine: body distribution and brain autoradiography: concise communication," *J. Nucl. Med.* 24(9):812-815 (Sep. 1983).

Hara, T., "$^{18}$F-fluorocholine: a new oncologic PET tracer," *J. Nucl. Med.* 42(12):1815-1817 (Dec. 2001).

Hara, T., "Transcript of Hara Talk," Publication information unknown.

Hara, T., et al., "Automated synthesis of [$^{11}$C]choline, a positron-emitting tracer for tumor imaging," *Appl. Rad. Isotopes* 50(3):531-533 (Mar. 1999).

Hara, T., et al., "Automated synthesis of fluorine-18 labeled choline analogue 2-fluoroethyl-dimethyl-2-oxyethylammonium," *J. NucL Med.* 156:44P (Jun. 1997).

Hara, T., et al., "Development of $^{18}$F-fluoroethylcholine for cancer imaging with PET: synthesis, biochemistry, and prostate cancer imaging," *J. Nucl. Med.* 43(2):187-199 (Feb. 2002).

Hara, T., et al., "Imaging of brain tumor, lung cancer, esophagus cancer, colon cancer, prostate cancer, and bladder cancer with (C-11)choline," *J. Nucl. Med.* 38(5 Suppl.):250P (1997).

Hara, T., et al., "PET Imaging of brain tumor with [*methyl*-$^{11}$C]choline," *J. Nucl. Med.* 38(6):842-847 (Jun. 1997).

Hara, T., et al., "PET imaging of prostate cancer using carbon-11-choline," *J. Nucl. Med.* 39(6):990-995 (Jun. 1998).

Hara, T., et al., "Sensitive detection of mediastinal lymph node metastasis of lung cancer with $^{11}$C-choline PET," *J. Nucl. Med.* 41(9):1507-1513 (Sep. 2000).

Hara, T., Translation of "Fluorine-18-labeled fluorine-containing choline derivatives, methods for their preparation, and their use as diagnostic agents for positron emission computed tomography," *Jpn. Pat. Off. Pat. J. Kokai Pat. App. No. HEI-9[1997]-48747*.

Hoh, C., et al., "Positron emission tomography in urological oncology," *J. Urol.* 159(2):347-356 (Feb. 1998).

Huang, Y., et al., "Synthesis and pharmacological characterization of a new PET ligand for the serotonin transporter: [$^{11}$C]5-bromo-2-[2-(dimethylaminomethylphenylsulfanyl)]phenylamine ([$^{11}$C]DAPA)," *Nucl. Med. Biol.* 29(7):741-751 (Oct. 2002).

Iwata, R., et al., "[$^{18}$F]Fluoromethyl triflate, a novel and reactive [$^{18}$F]fluoromethylating agent: preparation and application to the on-column preparation of [$^{18}$F]fluorocholine," *Appl. Rad. Isotopes* 57(3):347-352 (Sep. 2002).

Jalilian, A., et al., "A new method for one-step, no-carrier-added synthesis of cholesteryl 4-[$^{18}$F]-fluorobenzoate ([$^{18}$F]-CFB), a radiotracer used in detection of adrenal malignancies," *J. Pharm. Pharmaceut. Sci.* 3(1):114-124 (Jan.-Apr. 2000).

Kobori, O., et al., "Positron emission tomography of esophageal carcinoma using $^{11}$C-choline and $^{18}$F-fluorodeoxyglucose," *Cancer* 86(9):1638-1648 (Nov. 1999).

Miraldi, F., et al., "Elimination of artifactual accumulation of FDG in PET imaging of colorectal cancer," *Clin. Nucl. Med.* 23(1):3-7 (Jan. 1998).

Mishani, E., et al., "[C-11]choline-automated preparation and clinical utilization," *J. Labelled Cpd. Radiopharm.* 44(Supp. 1):S379-S381 (May 2001).

Moiseev, I.K., et al., "α-halo ketones in C-, N-, O-, and S-alkylation reactions," *Rus. J. Org. Chem.* 39(12):1685-1701 (Dec. 2003).

Moran, J., et al., "Optimization of urinary FDG excretion during PET imaging," *J. Nucl. Med.* 40(8):1352-1357 (Aug. 1999).

Mulholland, G.K., et al., "Convenient labeling and isolation of [$^{11}$C-methyl]quaternary amines," *J. Labelled Cpd. Radiopharm.* 42(Suppl. 1):S459-S461 (1999).

Musachio, J., et al., "Radiosynthesis and mouse brain distribution studies of [$^{11}$C] CP-126,998: a PET ligand for in vivo study of acetylcholinesterase," *Nucl. Med. Biol.* 29(5):547-552 (Jul. 2002).

Ogawa, M., et al., "Synthesis and in vivo evaluation of [$^{11}$C]methyl-Ro 64—6198 as an ORL1 receptor imaging agent," *Nucl. Med. Biol.* 28(8):941-947 (Nov. 2001).

Ravert, H., et al., "[$^{11}$C]-GR89696, a potent kappa opiate receptor radioligand; in vivo binding of the R and S enantiomers," *Nucl. Med. Biol.* 29(1):47-53 (Jan. 2002).

Roivainen, A., et al., "Blood metabolism of [*methyl*-$^{11}$C]choline; implications for in vivo imaging with positron emission tomography," *Eur. J. Nucl. Med.* 27(1):25-32 (Jan. 2000).

Rose, P., et al., "Positive emission tomography for evaluating a complete clinical response in patients with ovarian or peritoneal carcinoma: correlation with second-look laparotomy," *Gynecol. Oncol.* 82(1):17-21 (Jul. 2001).

Rosen, M., et al., "Carbon-11 choline: synthesis, purification, and brain uptake inhibition by 2-dimethylaminoethanol," *J. Nucl. Med.* 26(12):1424-1428 (Dec. 1985).

Schönbächler, R., et al., "PET imaging of dopamine transporters in human brain using [$^{11}$C]-β-CPPIT, a cocaine derivative lacking the 2β-ester function," *Nucl. Med. Biol.* 29(1):19-27 (Jan. 2002).

Shinoura, N., et al., "Brain tumors: detection with C-11 choline PET," *Radiology* 202(2):497-503 (Feb. 1997).

Szwergold, B., et al., "Characterization of a phosphonium analog of choline as a probe in $^{31}$P NMR studies of phospholipid metabolism," *NMR Biomed.* 7(3):121-127 (May 1994).

Taylor, M.D., et al., "[F-18] halothane photoaffinity labeling of bovine serum albumin (BSA)," *J. Nucl. Med.* 38(5):44P (May 1997).

Torizuka, T., et al., "Value of 11C choline PET imaging of malignant tumors in pelvis: Comparison with $^{18}$F-FDG PET," *J. Nucl. Med.* 42(5 Suppl.):287P (May 2001).

Weber, W., et al., "Relevance of positron emission tomography (PET) in oncology," *Strahlenther. Onkol.* 175(8):356-373 (Aug. 1999).

Chesis P. L., et. al., "N-(3-[$^{18}$F]Fluoropropyl)-N-nordiprenorphine: Synthesis and Characterization of a New Agent for Imaging Opioid Receptors with Positron Emission Tomography" *J. Med. Chem.*, vol. 33, No. 5, (1990).

Database Caplus 'Online! Chemical Abstracts Service, Columbus, Ohio, US; Block, Dirk: "Applied carrier-free 18F-fluoroalkylation and 18F-fluoroacylation" retrieved from STN Database accession No. 1988:204176 abstract & Ber. Kernforshungsanlage Juelich, Juel-2122, 131 PP. Coden: BKEJAS; (1987).

Hamacher K. et. al., "Efficient Sterospecific Synthesos pf No-Carrier-Added 2-[$^{18}$F]-Fluoro-2-Deoxy-D-Glucose using Aminopolyether Supported Nucleophilic Substitution" *Journal Of Nuclear Medicine*, Society Of Nuclear Medicine, New York, US vol. 27, No. 2, (Feb. 1986).

Iwata, R. et. al., "Radiosynthesis of 0-[$^{11}$C]methyl-L-tryosine and 0-[$^{18}$F]Fluoromethyl-L-tyrosine as potential PET tracers for imaging amino acid transport" *J. Label Compd. Radiopham*, vol. 46, May 2003.

Kiesewetter, D. et. al., Radiochemical Synthesis of [$^{18}$F]Fluororaclopride, *International Journal of Radiation Applications and Instrumentation Part A: Applied Radiation and Isotopes*, vol. 40, No. 6, (Jan. 1989).

Lim, J. L. et. al., "Automated Production of [$^{18}$F]FECh and [$^{18}$F]FCH: Preparation and Use of [$^{18}$F]Fluoroalkane Sulfonates as Fluoroalkylation Agents" *J. Label Compd. Radiopharm.*, vol. 46, (Aug. 2003).

Zhang, J. et. al., "Synthesis and Evaluation of Two Positron-Labeled Nitric Oxide Synthase Inhibitors, S-[$^{11}$C]Methylisothiourea and S-(2-[$^{18}$F]Fluorethyl) isothiourea, as Potential Positron Emission Tomography Tracers" *J. Med Chem.*, vol. 39, No. 26, (1996).

Zhang, M-R et. al., "N-[$^{18}$F]fluoroethyl-4-piperidyl Acetate ([$^{18}$F]FEtP4A): A PET Tracer for Imaging Brain Acetylchlolinesterase In Vivo" *Bioorg, Med. Chem.*, vol. 11 (Jun. 2003).

Zhang, M-R, et. al., "Development of an automated system for synthesizing $^{18}$F-labeled compounds using [$^{18}$F]fluorothyl bromide as a synthetic precursor" *Applied Radiation And Isotopes*, Pergamon Press Ltd., Exeter, GB, vol. 57, No. 3, (Sep. 2002).

* cited by examiner

MQNB

_US 7,776,309 B2_

PREPARATION AND USE OF ALKYLATING AGENTS

1. CROSS-REFERENCE TO RELATED APPLICATION

This application claims the benefit of the filing date under 35 U.S.C. 119(e) of U.S. Patent Application Ser. No. 60/490,233, filed Jul. 24, 2003, expressly incorporated by reference.

2. FIELD

This invention relates, generally, to organic chemistry and more particularly to processes for synthesizing alkylating agents and methods of use.

3. BACKGROUND

Alkylation processes have been used to synthesize and modify myriad compounds (see, e.g., U.S. Pat. Nos. 6,277,982, 6,278,020, 6,281,380, 6,281,399, 6,281,405, 6,288,233, 6,291,716, 6,291,724, 6,294,499, 6,303,840, 6,307,048, 6,313,362, 6,315,964, 6,339,179, 6,355,839, 6,376,729, 6,376,730, 6,387,705, 6,388,157, 6,392,114, 6,395,871, 6,395,945, 6,423,871, 6,429,349, 6,440,886, 6,448,458, 6,479,721, 6,486,374, 6,492,571, 6,500,998, 6,504,071, 6,512,153, 6,515,169, 6,525,234, 6,528,316, 6,541,655, 6,548,113, 6,552,241, 6,555,722, 6,642,425, 6,642,426, 6,664,432, 6,673,977, 6,677,269, 6,709,638, 6,747,152, 6,750,354, 6,759,349). These processes typically require multiple steps of synthesis and purification of reaction intermediates and/or the removal of unwanted byproducts. Therefore, these processes can be unsuitable or of limited use for the synthesis or modification of radiolabeled compounds, especially when the radioisotope is relatively short lived and the radiolabeled compound is intended for use as a radiotracer or imaging agent. Thus, there is a need in the art for rapid and efficient alkylation processes that can be used for the synthesis or modification of radiolabeled compounds.

Therefore, the present disclosure provides compositions and methods to rapidly and efficiently alkylate target compounds, which may be used for the synthesis or modification of radiopharmaceuticals.

4. SUMMARY

The present disclosure provides methods of alkylating a target compound comprising one or more alkylation reactive groups. In some embodiments, the methods comprise synthesizing an alkylating agent. In some embodiments, the alkylating agent may comprise one or more leaving groups and an alkylation moiety. In some optional embodiments, the alkylating agent may comprise a detectable moiety. In some embodiments, the alkylation moiety may comprises a detectable moiety. In some embodiments, the detectable moiety may be a radioisotope.

In some embodiments, an alkylating agent can be utilized in an alkylation reaction without an intervening purification step. Therefore, in some embodiments, an alkylating agent, once synthesized, can be used to directly alkylate a target compound. In some embodiments, the synthesis of an alkylating agent and alkylation of a target compound may occur in a single vessel.

In some embodiments, various aspects of the disclosed methods can be automated by a general purpose or special purpose device. In some embodiments, the device may comprise a processor or computer for storing data and/or executing computer program code instructions. Therefore, in some embodiments a computer readable memory to direct a computer to function in specified manner can be utilized. The computer or processor may control any one or more aspects of the disclosed methods.

In other aspects of the disclosure are provided alkylated and/or labeled target compounds. In some embodiments, the target compounds can be labeled with a radioactive detectable moiety. Therefore, in some embodiments the alkylated and/or labeled target compounds may be used a therapeutic, tracers, and or imaging agents either in vitro or in vivo. In some embodiments, an labeled target compound can be used as an imaging agent for positron emission tomography.

5. BRIEF DESCRIPTION OF THE DRAWINGS

Figure 10:
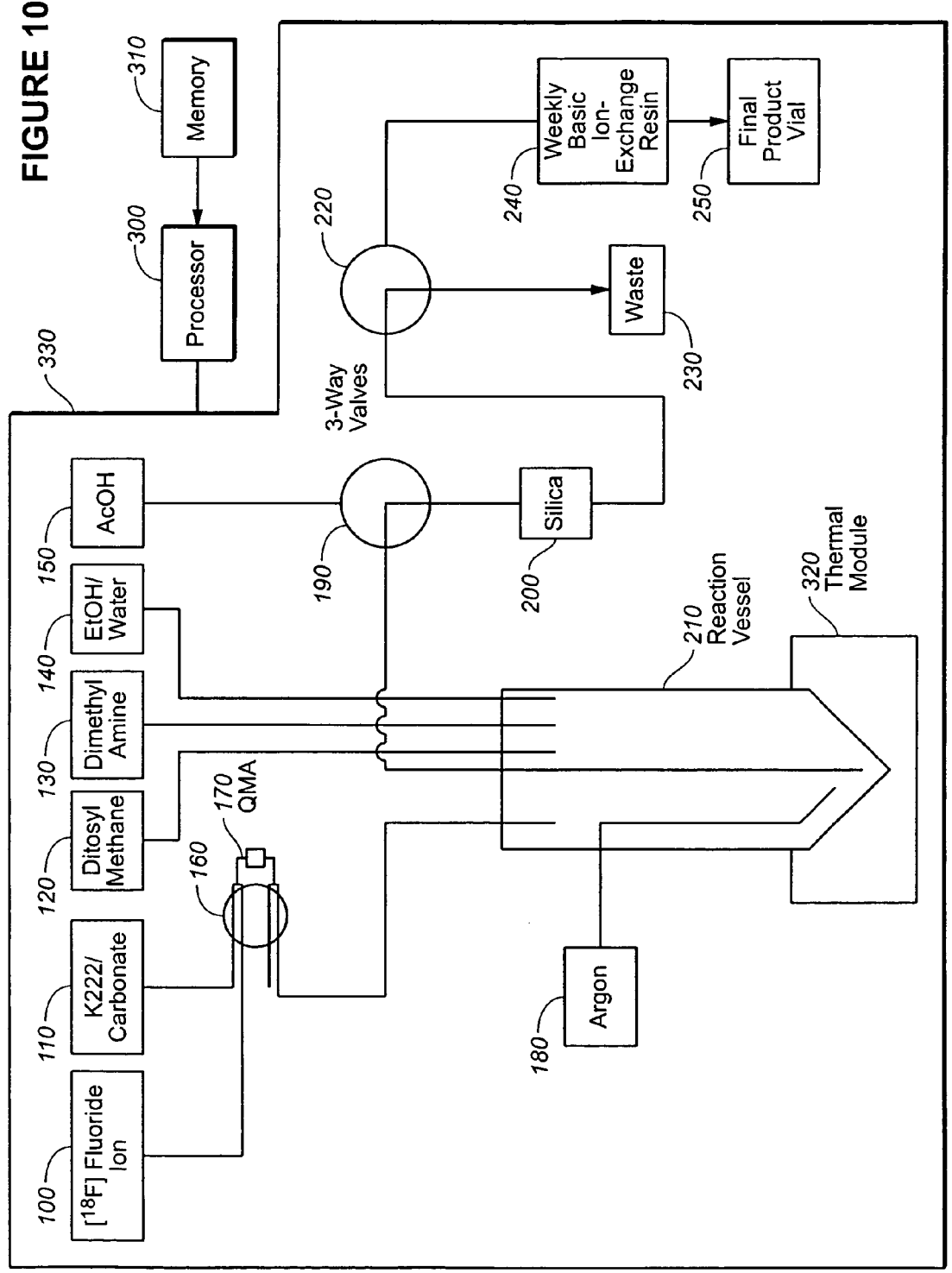

FIG. 10 provides a schematic illustrating a system suitable for automated synthesis of an alkylating agent, the alkylation of a target compound ($T_c$) and the purification of an alkylated target compound, according to one embodiment.

Figure 11:
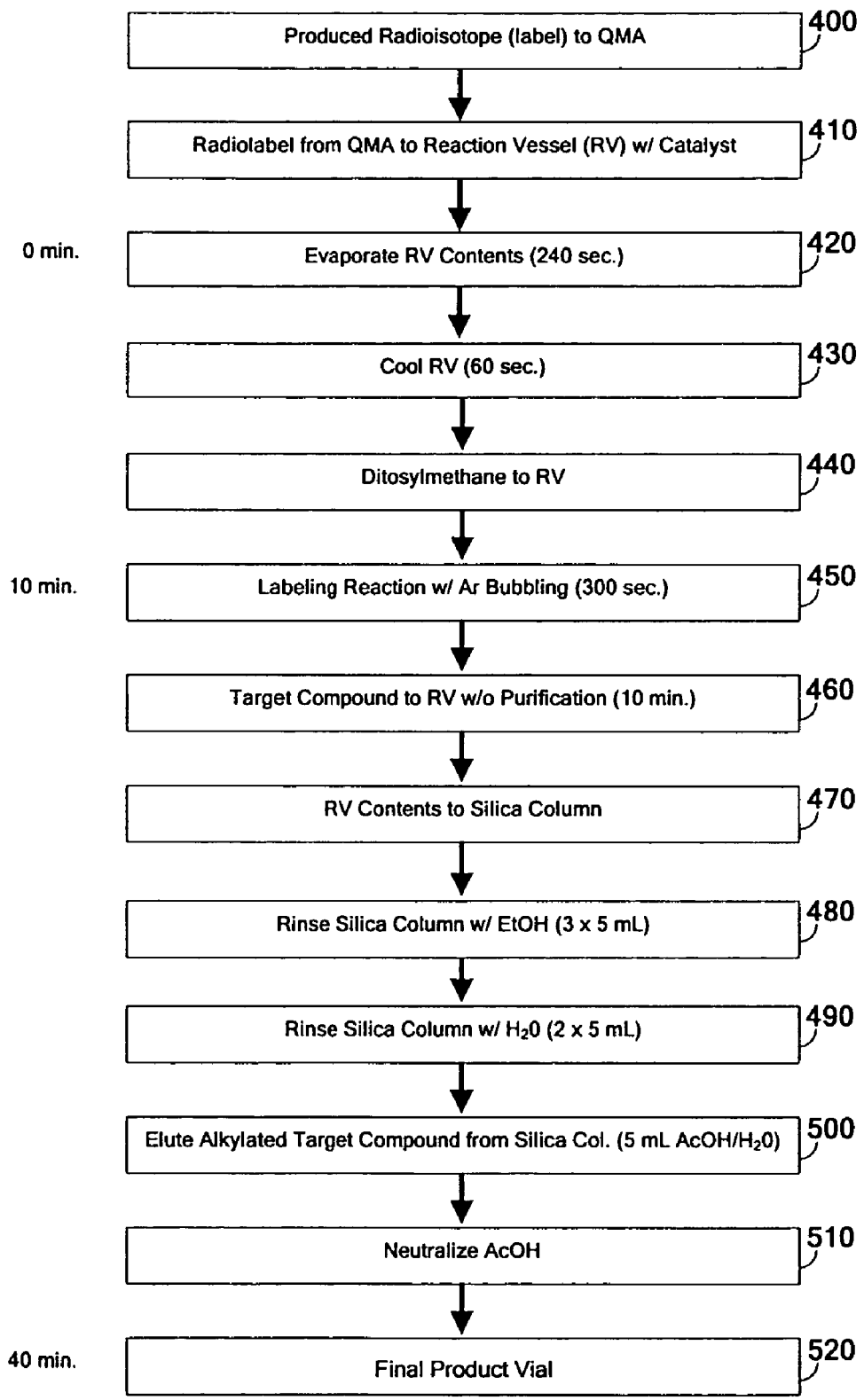

FIG. 11 provides a flow diagram of the synthesis of an radioalkylated target compound, according to one embodiment. The numbers to the left of the diagram indicate the approximate time point of the exemplified synthesis.

Figure 12:
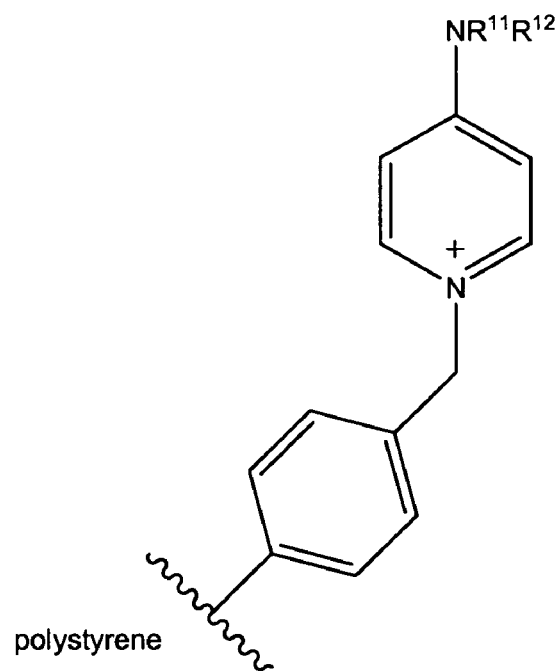

FIG. 12 depicts a structure of a polymer resin containing a covalently attached quaternary ammonium salt, polystyrene 4-dialkylaminopyridinium, according to one embodiment, wherein $R^{11}$ and $R^{12}$ are alkyl groups.

Figure 13:
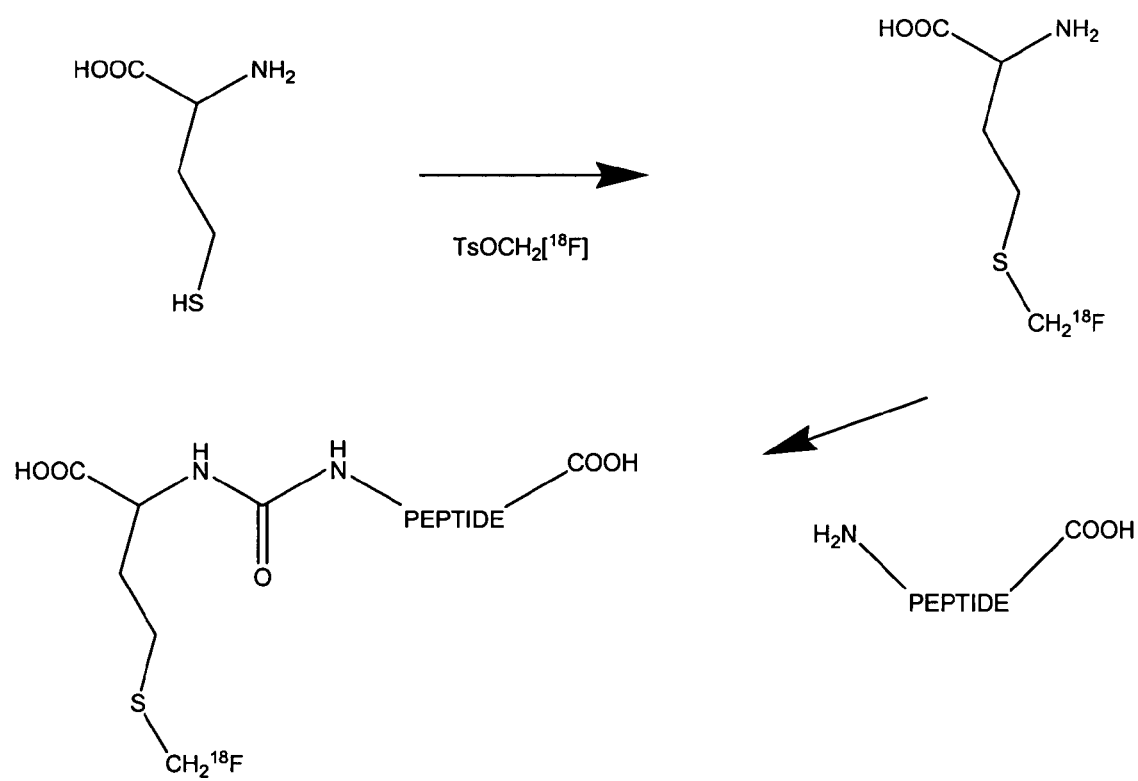

FIG. 13. depicts the [$^{18}$F]fluoroalkylation of cysteine to produce [$^{18}$F]-labeled methionine and the linkage of the [$^{18}$F]-labeled methionine to the amino terminus of a peptide according to one embodiment.

Figure 14:
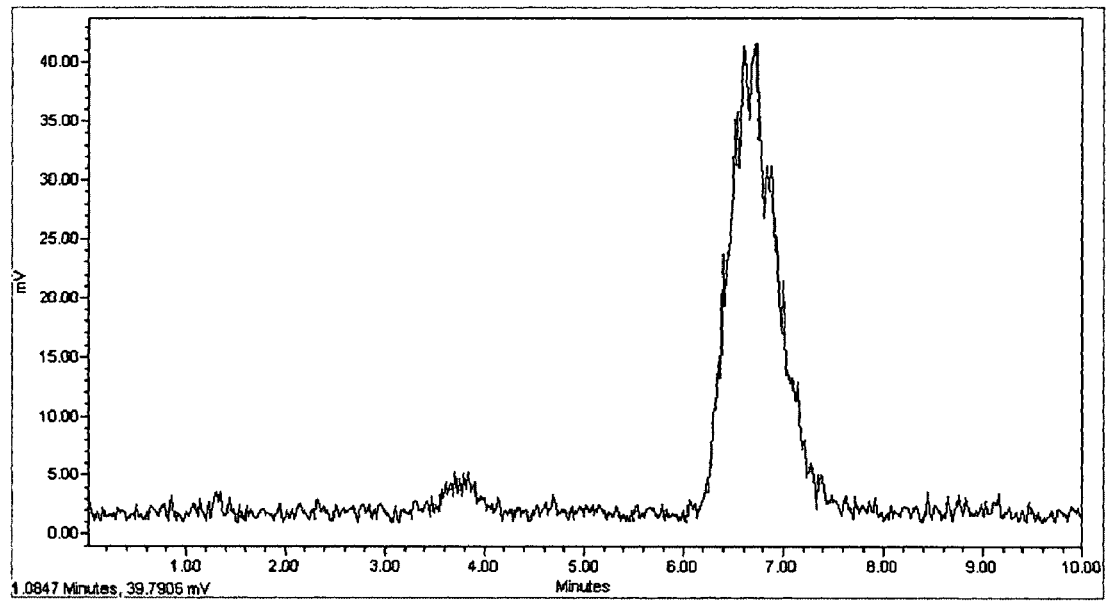

FIG. 14 shows an HPLC tracing of [$^{18}$F]FECh using a radioactivity detector (mV vs. min.), according to one embodiment. The tracing shows a major radioactive peak, [$^{18}$F]FECh.

Figure 15:
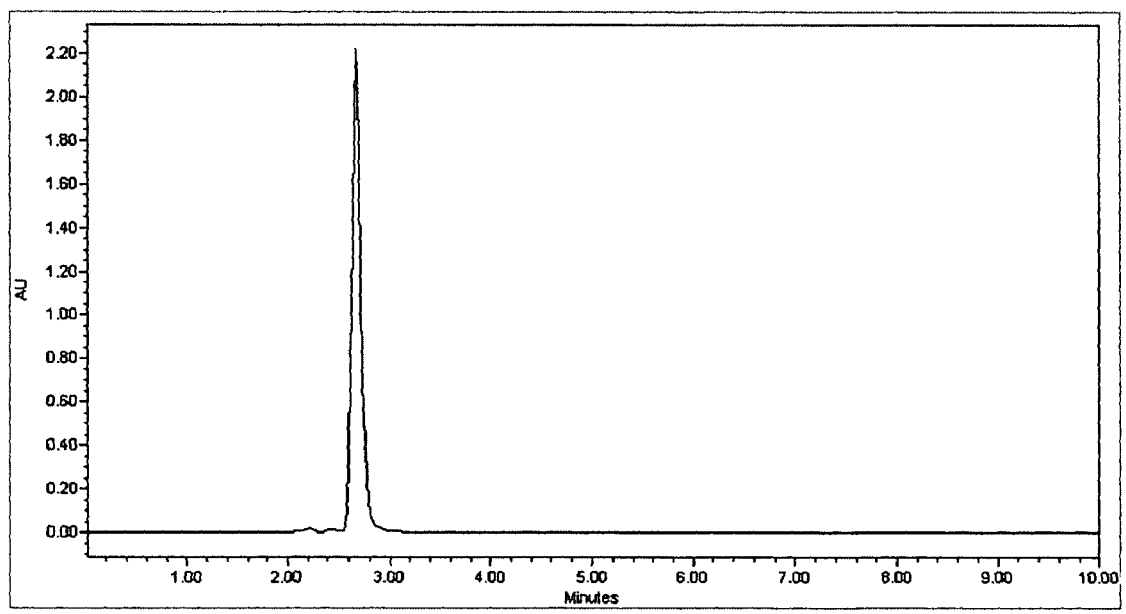

FIG. 15 shows an HPLC tracing of [$^{18}$F]FECh using an ultraviolet (UV) detector (Absorbance Units (AU) vs. time), according to one embodiment. The tracing shown a major peak detectable by UV absorbance, dimethylethanolamine. [$^{18}$F]FECh is not detectable by UV absorbance.

Figure 16:
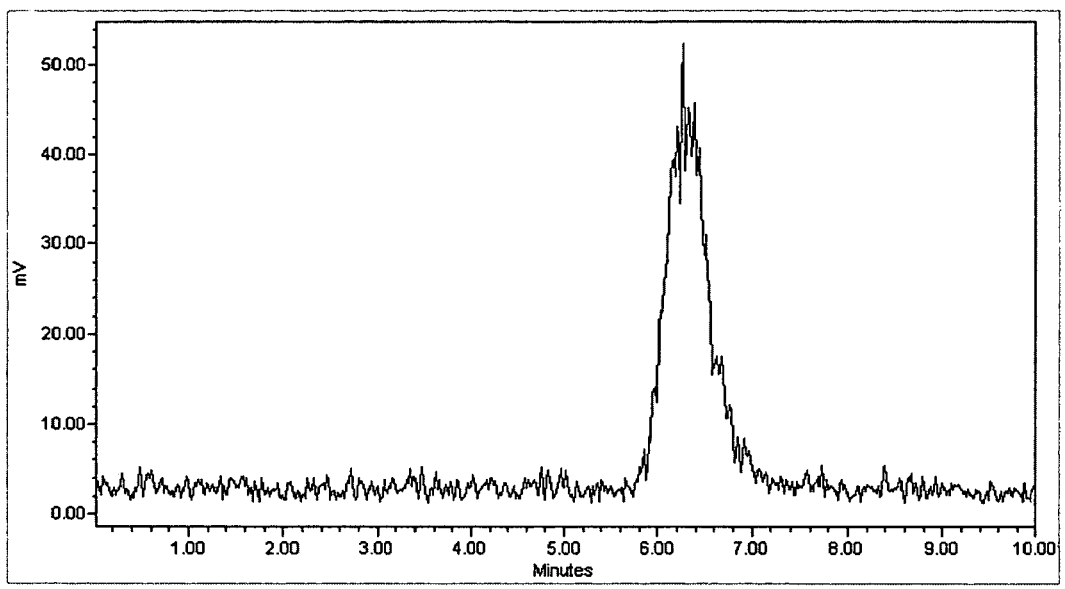
Figure 17:
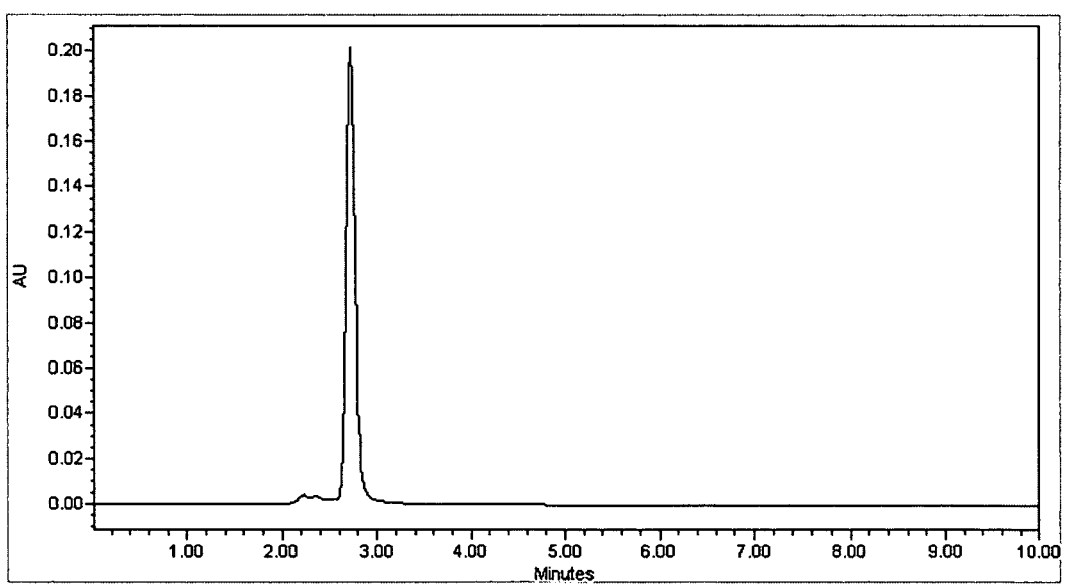

FIG. 16 shows an HPLC tracing of [$^{18}$F]FCH using a radioactivity detector (mV vs. min.), according to one embodiment. The tracing shows a major radioactive peak, [$^{18}$F]FCH, FIG. 17 shows an HPLC tracing of [$^{18}$F]FCH using a radioactivity detector (mV vs. min.), according to one embodiment. The tracing shown a major peak detectable by UV absorbance, dimethylethanolamine. [$^{18}$F]FCH is not detectable by UV absorbance.

6. DETAILED DESCRIPTION

The present disclosure is directed to the discovery of methods of synthesizing an alkylating agent and alkylating a target compound. In some embodiments, the alkylating agent can be labeled. In some embodiments, the label can be transferred to a target compound in an alkylation reaction. In some embodiments, an alkylated target compound finds use as a tracer molecule, imaging agent or therapeutic. Thus, in some embodiments, a labeled alkylated target compound can be a radiopharmaceutical that can be used to determine the metabolic or physiologic status of a cell or tissue in vivo or in vitro. Therefore, in some embodiments the present disclosure provides methods of detecting or monitoring a radioactive compound in a tissue or cell. In some embodiments, the detected or monitored radioactive compound can be used to assess the metabolic or physiologic status of a cell or tissue.

In some embodiments, the disclosed methods comprise synthesizing an alkylating agent and the alkylation of a target compound in a single reaction vessel. In some embodiments, the synthesis and alkylation reactions can be a coupled procedure without an intervening purification step. In some embodiments, the methods further comprise isolating or purifying an alkylated target compound.

In some embodiments, one or more aspects of the disclosed methods can be automated. Thus, in various embodiments, the disclosure provides one or more automated modules each capable of performing and/or providing reaction conditions suitable for one or more steps of the disclosed methods. In some embodiments, one or more modules can be controlled by a device having a processor for storing data and/or commands.

"Alkylating agent", "alkylation agent" and grammatical equivalents herein refer to compounds having a moiety suitable for forming an alkyl group that can be transferred to an alkylation reactive center or group of another compound, e.g., a target compound, in an alkylation reaction. By "alkylation reaction", "alkylating", "alkylation" and grammatical equivalents herein are meant a reaction in which an alkyl group is transferred to an alkylation reactive center or group of a compound by substitution and/or addition. Thus, in some embodiments an alkyl group can be transferred to an alkylation reactive center of a target compound to form an alkylated target compound. By "alkylation reactive center", alksylation reactive group" and grammatical equivalents herein are meant at least one atom of a compound that reacts with an alkylating agent in a process in which an alkyl group can be transferred to the compound from the alkylating agent. In some embodiments, an "alkyl group" and grammatical equivalents herein refers to any of a series of univalent groups of the general formula $C_nH_{(2n+1)}$. Thus, in various exemplary embodiments an alkyl group can be methyl, ethyl, propyl, isopropyl, $C_2H_3$ and the like, and as further described below. In some embodiments, an alkyl group may further comprise a detectable moiety.

In various exemplary embodiments, an alkylation reaction may comprise a nucleophilic attack of an alkylation reactive center of a target compound to an electron deficient region of an alkylating agent according to an $SN_1$ or $SN_2$ mechanism, as known in the art (see, e.g., Jerry March, *Advanced Organic Chemistry: Reactions, Mechanisms, and Structure*. 293-871 (4$^{th}$ ed. John Wiley & Sons 1992)). Therefore, the skilled artisan will appreciate that in some embodiments, an alkylating agent further comprises one or more leaving groups (LGs). By "leaving group" and grammatical equivalents herein are meant an atom or molecule that detaches from a molecule, e.g., an organic molecule. In some embodiments, the residual part can be the alkyl group which becomes covalently bonded to a target compound. Accordingly, in various exemplary embodiments, a leaving group can be an atom or group, charged or uncharged, that becomes detached from an atom or molecule in what is considered the residual or main part of the substrate in a specified reaction. The ability of a leaving group to leave the alkylating agent can be a function of the leaving group's lability. Thus, a leaving group can affect the intrinsic reactivity of the alkylating agent in an alkylation reaction. In some embodiments, the lower the pKa of the conjugate acid of the leaving group, the better the leaving group, because, in some embodiments, the leaving group can more easily stabilize the developing negative charge that can occur in an alkylation reaction. Therefore, in some embodiments, a leaving group can be an electronegative atom or molecule. Examples of leaving groups include, but are not limited to, acetate (AcO), p-nitrobenzoate (PNBO), sulfonates (e.g., methanesulfonate (Mesylate: MsO), p-toluenesulfonate (tosylate: TsO), p-bromobenzenesulfonate (Brosylate: BsO), p-nitrobenzenesulfonate (Nosylate: NsO), fluoromethanesulfonate, difluoromethanesulfonate, trifluoromethanesulfonate (Triflate: TfO) and ethanesulfonate), $NH_3$, halide esters, halogen ions (e.g., I$^-$, Br$^-$, Cl$^-$) and $H_2O$. Therefore, in various exemplary embodiments, alkylation agents include but are not limited to (TsO)$_2$CH$_2$, (TsO)CH$_3$, (TsO)$_2$C$_2$H$_5$, (TsO)$_2$C$_3$H$_7$, (MsO)C$_2$H$_5$, (I)$_2$CH$_2$, (I)CH$_3$, (I)$_2$C$_2$H$_5$, (I)$_2$C$_3$H$_7$, (I)C$_2$H$_5$, (Br)$_2$CH$_2$, (Br)CH$_3$, (Br)$_2$C$_2$H$_5$, (Br)$_2$C$_3$H$_7$, (Br)C$_2$H$_5$, and the like.

In some embodiments, an alkylating agent comprises one or more labels. In some embodiments, the a group or moiety suitable for transfer to a target compound (i.e., an alkylation moiety) comprises one or more labels. By "label", "detectable moiety", and grammatical equivalents herein are meant any distinguishing feature of a molecule or compound suitable for detecting or monitoring. Accordingly, a label may be an inherent feature of a compound and/or a moiety attached either covalently or non-covalently to a compound. Labels are well-known in the art and are chosen at the discretion of the practitioner based on the method of synthesizing, using and/or detecting a compound comprising the label. The skilled artisan will appreciate that in some embodiments a label does not substantially interfere or inhibit a function or an activity of the compound comprising the label. Therefore, in some embodiments a label of an alkylating agent may not substantially interfere with the alkylation of another compound, e.g., a target compound, by the alkylating agent. Determining the degree or extent to which a label may interfere with an activity or function of a compound to which it can be attached is within the abilities of the skilled artisan.

In various exemplary embodiments, labels include but are not limited to, a fluorophore (e.g., Richard P. Haugland, *Handbook of Fluorescent Probes and Research Chemicals Sixth Edition* (Michelle T. Z. Spence, ed., Molecular Probes, Inc. 1996), expressly incorporated by reference); a ligand (e.g., a hapten, biotin), a mobility modifier (e.g., U.S. Pat. Nos. 5,470,705, 5,514,543, 6,395,486, expressly incorporated by reference), an encoded microbead (e.g, U.S. Pat. Nos. 6,630,307, 6,500,622, 6,274,323, expressly incorporated by reference), an enzymatic label, organic or inorganic compounds, a radiolabel (e.g., $^{18}$F, $^{11}$C, $^{14}$C, $^{123}$I, $^{124}$I, $^{125}$I, $^{131}$I, $^{76}$Br), or combinations thereof. In some embodiments, a radiolabel preferably has a high specific activity, such as, at least about 600 mCi/mmol or higher and/or a short positron range, such as, from about 2 mm to about 5 mm. In some embodiments, the position range can be less than about 2 mm. Accordingly, in some embodiments, a radiolabel can be a suitable positron emitter for radioimaging techniques including but not limited to positron emission tomography (PET).

In some embodiments, an alkylating agent has the structure of Formula I and comprises an alkylation moiety, a leaving group and a label:

$$X(CR^1R^2)_aCR^3R^4\text{-LG} \qquad (I)$$

wherein,
a is an integer from 0 to 3;
$R^1$, $R^2$, $R^3$, and $R^4$ are independently H, X, or alkyl;
X is a H, a halogen, or a label; and
LG is a leaving group.
In some embodiments:
a is 1;
$R^1$, $R^2$, $R^3$, and $R^4$ are H;
X is a $^{18}$F, $^{123}$I, $^{124}$I, $^{125}$I, $^{131}$I or $^{76}$Br; and
LG is a sulfonate ester.
In some embodiments:
a is 0;
$R^3$ and $R^4$ are H;
X is [$^{18}$F]; and
LG is tosylate, mesylate or triflate.
In some embodiments:
a is 0;
$R^3$ and $R^4$ are H or X;
X is [$^{18}$F]; and
LG is tosylate, mesylate or triflate.

Thus, in various exemplary embodiments, alkylating agents comprising radiolabels include but are not limited to haloalkylsulfonates, such as, [$^{18}$F]fluoroalkylsulfonates (e.g., [$^{18}$F]fluoroethane sulfonates (e.g., [$^{18}$F]fluoroethane tosylate, [$^{18}$F]fluoroethane mesyltate, [$^{18}$F]fluoroethane triflate), [$^{18}$F]fluoromethane sulfonates (e.g., [$^{18}$F]fluoromethane tosylate, [$^{18}$F]fluoromethane mesylate, [$^{18}$F]fluoromethane triflate)), [$^{76}$B]bromoalkylsulfonates (e.g., [$^{76}$B]bromoethane sulfonates (e.g., [$^{76}$B]bromoethane tosylate, [$^{76}$B]bromoethane mesyltate, [$^{76}$B]bromoethane triflate), [$^{76}$B]bromomethane sulfonates (e.g., [$^{76}$B]bromomethane tosylate, [$^{76}$B]bromomethane mesylate, [$^{76}$B]bromomethane triflate)), [$^{125}$I]iodoalkylsulfonates (e.g., [$^{125}$I]iodoethane sulfonates (e.g., [$^{125}$I]iodoethane tosylate, [$^{125}$I]iodoethane mesyltate, [$^{125}$I]iodoethane triflate), [$^{125}$I]iodomethane sulfonates (e.g., [$^{125}$I]iodomethane tosylate, [$^{125}$I]iodomethane mesylate, [$^{125}$I]iodomethane triflate)), and the like.

In various exemplary embodiments, alkylating agents find use in methods of alkylating or labeling a target compound. "Target compound" and grammatical equivalents herein refer to a compound comprising one or more alkylation reactive centers and, accordingly, can be alkylated by any one or more alkylating agents, either alone or in any combination, by the methods disclosed herein. In some embodiments, two or more target compounds may be alkylated by any one or more alkylating agents either simultaneously and/or sequentially. Determining the suitability of one or more target compounds or one or more alkylation reactive centers for alkylation by any one or more alkylating agents either simultaneously or sequentially is within the abilities of the skilled artisan. In some embodiments, a target compound comprises a label, as described above. Accordingly, in some embodiments, a label does not substantially interfere with or inhibit the alkylation and/or use of the alkylated target compound.

In some embodiments, the alkylation reactive center or group of a target compound can be a suitable nucleophile for an alkylation reaction. Examples of alkylation reactive centers include but are not limited to a N, O, S, P, C, aldehydes, aliphatic carbons, alkanes, alkenes, alkynes, alcohols (—OH), amines (e.g., primary, secondary, tertiary and quaternary amines), aromatic compounds (e.g., benzene, phenyl), carboxylic acids (—COOH), esters, diazonium ions, dithianes, enamines, enolates, heterocycles, hydrazones, imines, ketones, nitriles, oxazines, oxazolines, selenoxides, sulfones, sulfonates, and cyclic, linear, and branched, and substituted and unsubstituted derivatives thereof. *Dictionary of Chemical Terms* (Parker, et al. eds., McGraw-Hill Book Co.), *Encyclopedia of Chemistry* (Considine, et al. eds., 4th ed., Van Nostrand Reinhold Co.), March, *Advanced Organic Chemistry*), expressly incorporated by reference. In a some embodiments, an alkylation reactive group can be an alkyl, substituted alkyl, saturated and unsaturated cycloalkyl, aryl, substituted aryl, sulhydryl (—SH), amino, and saturated and unsaturated heterocycles comprising, for example, one or more of nitrogen, oxygen, sulfur, and combinations thereof.

By "alkyl group" herein is meant a saturated or unsaturated, branched, straight-chain or cyclic monovalent hydrocarbon group derived by the removal of one hydrogen atom or leaving group from a single carbon atom of a parent alkane, alkene or alkyne. If branched, it may be branched at one or more positions and unless specified at any position. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc., and the like.

Thus, in some embodiments, "alkyl groups" refers to groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In various exemplary embodiments, an alkyl group comprises from about 1 to about 20 carbon atoms ($C_1$-$C_{20}$ alkyl), from about 1 to about 15 carbon atoms ($C_1$-$C_{15}$ alkyl), from about 1 to about 10 carbon atoms ($C_1$-$C_{10}$ alkyl), or from about 1 to about 6 carbon atoms ($C_1$-$C_6$ alkyl), or from about 1 to about 3 carbon atoms ($C_1$-$C_3$).

The term "substituted alkyl group" refers to an alkyl group as defined above in which one or more of the hydrogen atoms can be replaced by a substituent group, for example, a halide (e.g. F, Br, I, Cl), alkyl, amine, aromatic compound, aryl, hydroxyl, carbonyl, diazo, imines, nitrile, nitro, sulhydryl and sulfonyl.

The term "cycloalkyl group" refers to an alkyl group as defined above having cyclic structure having up to about 20 carbon atoms ($C_{20}$). In various exemplary embodiments a cycloalky can be mono- or polycyclic, e.g., bicyclic. A cycloalkyl group may optionally contain one or more carbon-carbon double bounds provided that the group is not aromatic. Therefore, in various exemplary embodiments a cycloalky group can be saturated or unsaturated.

As used herein "aryl group" refers to an aromatic monocyclic or polycyclic hydrocarbon group containing about 6 to about 20 carbon atoms ($C_6$-$C_{20}$ aryl), from about 6 to about 15 carbon atoms ($C_6$-$C_{15}$ aryl) or from about 6 to about 10 carbon atoms ($C_6$-$C_{10}$ aryl) and any carbocyclic ketone or thioketone derivative thereof, wherein the carbon atom with the free valence is a member of an aromatic ring, (e.g., aryl includes phenyl, naphthyl, anthracenyl, phenanthrenyl, 1,2,3,4-tetrahydro-5-naphthyl, 1-oxo-1,2-dihydro-5-naphthyl, 1-thioxo-1,2-dihydro-5-naphthyl, etc.).

In some embodiments, an aryl can be a heteroaryl. "Heteroaryl group" refers to aromatic monocyclic or polycyclic hydrocarbon group containing overall from 6 to 20 atoms, wherein at least 1 to about 5 of the indicated carbon atoms are replaced by a heteroatom chosen from N, O, S, P or As, wherein the atom with the free valence is a member of an aromatic ring, and any heterocyclic ketone and thioketone derivative thereof (e.g., thienyl, furyl, pyrrolyl, pyrimidinyl, isoxazolyl, oxaxolyl, indolyl, benzo[b]thienyl, isobenzofuranyl, purinyl, isoquinolyl, pterdinyl, pyrimidinyl, imidazolyl, pyridyl, pyrazolyl, pyrazinyl, 4-oxo-1,2-dihydro-1-naphthyl, 4-thioxo-1,2-dihydro-1-naphthyl, etc.). Thus, hetero($C_6$)aryl includes the groups pyridyl, pyrimidinyl, and the like.

In some embodiments, an aryl can be a substituted aryl. "Substituted aryl group" refers to an aryl group as defined above in which one or more of the hydrogen atoms can be replaced by a substituent group, for example, a halide (e.g. F, Br, I, Cl), alkyl, amine, aromatic compound, aryl, hydroxyl, carbonyl, diazo, imines, nitrile, nitro, sulhydryl and sulfonyl.

As used herein, "heterocycle" refers to ring composed of atoms of more than one kind. Therefore, in some embodiments a heterocycle includes but is not limited to a carbon ring having at least one other kind of atom in the ring. In various exemplary embodiments a heterocycle can be saturated or unsaturated. In some embodiments, heteroatoms can be attached to the ring structure. In some embodiments, a heterocycle can have up to 20 atoms in one or more rings. Therefore, in various exemplary embodiments a heterocycle can mono- or polycyclic, e.g., bicyclic.

Accordingly, in various exemplary embodiments, a target compound may comprise an organic compound, an inorganic compound, a naturally occurring compound (e.g., isolated from nature (e.g., polypeptide, a nucleic acid, a hormone, a cytokine, an antibody and the like), a non-naturally occurring compound (e.g., synthetic or not known to occur in nature, e.g., peptide nucleic acids (PNA), a pharmaceutical (e.g., an antiviral, a pro-drug) and/or combinations thereof. In some embodiments, a target compound can be a biological compound. By "biological compound", "biochemical compound" and grammatical equivalents herein are meant a compound having at least one biological or biochemical activity in vivo (e.g., in a subject) or in vitro (e.g., in tissue culture or in an assay). Therefore, in various exemplary embodiments a biologically active compound may specifically or non-specifically bind to another molecule and/or cell and/or enter a cell of interest. In some embodiments, a cell may be a prokaryotic cell, a eukaryotic cell (e.g., a tumor cell), a corpuscle, an anucleate cell, an enucleate cell and the like. In various exemplary embodiments, binding can be to a molecule (e.g., an antibody or binding fragment thereof), a class of molecules (e.g., MHC Class II molecules), a specific receptor or class of receptors and the like. In some embodiments, a biologically active compound preferably traverses one or cellular membrane(s) and/or cellular walls. In some embodiments, a biologically active compound may accumulate in a cellular organelle or region (e.g., cytoplasm, mitochondria, endoplasmic reticulum, one or more surfaces of a membrane etc.). A biologically active compound may enter a cell by various mechanisms, such as, active or passive mechanisms. These mechanisms include but are not limited to, diffusion and endocytic mechanisms, e.g., receptor-mediated endocytosis, and active and passive transport. In some embodiments, a biologically active compound is taken up by a cell of interest at a rate or magnitude that substantially exceeds other cells. Thus, the present disclosure contemplates biologically active compounds that enter a cell of interest at a rate that exceeds other cells and biologically active compounds that accumulate in a cell of interest at a final concentration that exceeds the concentration in other cells. For example, in some embodiments, a biological compound may preferentially enter a tumor cell in comparison to a non-tumor cell.

In some embodiments, upon entry into a cell, a biologically active compound can be metabolized by the cell, whereby the hydrophobicity of the biologically active compound can be altered. In some embodiments, the hydrophobicity of the biologically active compound, once modified, is decreased to facilitate retention of the compound in a cell. The hydrophobicity of the biologically active compound may be decreased by a number of cellular processes, such as, the addition of a polar (e.g., hydroxyl) or charged group (e.g., phosphate, carboxylate), by oxidation (e.g., conversion of an hydroxyl group to a carbonyl), or by the removal of a hydrophobic group (e.g., alkyl). The method by which the hydrophobicity of a biologically active compound can be decreased is within the abilities of the skilled artisan and can be based on the biologically active compound and the metabolic process of the cell of interest.

Examples of biologically active compounds include but are not limited to choline, dimethylethanolamine (DeGrado, et al. (2001) *J. Nucl. Med.* (42:1805-1814); U.S. Pat. No. 6,630, 125; Hara, et al. (2002) *J. Nucl. Med.* 43(2):187-199; Hara, et al. Japanese Patent Office, Patent Journal (A), Kokai Patent Application No. HEI 9[1997]48747), morphine, heroin, pethine, tamoxifen, codeine, nicotine, thioperazine, diazepam, caffeine, flunitrazepam, hexamethonium, methiodide, quinuclidinyl benzilate, glucose, deoxyglucose, lactic acid, hexobarbital, thymidine, iodoantipyrine, antipyrine, coenzyme Q, adenosylmethionine, phenylamines (Huang, et al. (2002) *Nuc. Med. Biol.* 29(741-751), CP-126,998 (Musachio, et al. (2002) *Nucl. Med. Biol.* 29:547-552), cocaine derivatives (Schönbächler, et al. (2002) *Nucl Med. Biol.* 29:19-27), proteins and peptides (U.S. Pat. No. 6,358,489), neurokinin-1 receptor antagonists (U.S. Pat. Nos. 6,241,964, 6,187,284), spiroperidols (U.S. Inv. Reg. H1209, U.S. Pat. No. 4,871, 527), fatty acids (U.S. Pat. No. 6,362,352), platelet GPIIb/IIIa receptor antagonists (U.S. Pat. Nos. 5,879,657, 6,022,523), fluoromisonidazole (U.S. Pat. No. 5,886,190), tamoxifen derivatives (U.S. Pat. No. 5,219,548), opioid ligands (U.S. Pat. No. 4,775,759; Ravert, et al. (2002) *Nucl. Med. Biol.* 29:47-53; Ogawa, et al. (2001) *Nucl. Med. Biol.* 28:941-947), non-steroidal aromatic compounds (U.S. Pat. No. 6,019,957), amino acid analogs (U.S. Pat. Nos. 5,187,776, 5,808,146), MQNB, neostigmine, MPP, NMS, amino acids (e.g., tyrosine (e.g., —OH), serine (e.g., —OH), threonine (e.g., —OH), cysteine (e.g., thio), aspartic acid (e.g., —COOH), glutamic acid (e.g., —COOH), carboxylic acids (e.g., benzoic acid and amino acids), spiperone, spiroperidol.

An alkylating agent can be synthesized from a disubstituted alkyl precursor. Therefore, in some embodiments, a precursor of an alkylating agent may have the structure of Formula II:

$$LG^1\text{-}(CR^1R^2)_a CR^3R^4\text{-}LG^2 \qquad (II)$$

wherein, a is 0 to 2;

$R^1, R^2, R^3$, and $R^4$ are independently H, a label, $CH_3, C_2H_3$; and $LG^1$ and $LG^2$ are leaving groups.

In some embodiments:

a is 0 to 1;

$R^1, R^2, R^3$, and $R^4$ are H; and $LG^1$ and $LG^2$ are sulfonate esters or $^{18}F, ^{123}I, ^{124}I, ^{125}I, ^{131}I, ^{76}Br$.

In some embodiments:

a is 0 to 1;

$R^1, R^2, R^3$, and $R^4$ are H; and $LG^1$ and $LG^2$ are independently tosylate, mesylate or triflate.

In some embodiments:

a is 1;

$R^1, R^2, R^3$, and $R^4$ are H; and $LG^1$ and $LG^2$ are both tosylate, mesylate or triflate.

In some embodiments:

a is 0;

$R^3$, and $R^4$ are H; and $LG^1$ and $LG^2$ are both tosylate, mesylate or triflate.

Thus, in various exemplary embodiments, a precursor of an alkylating agent includes but is not limited to disulfonate esters, e.g., ditosylethane, dimesylethane, ditriflylethane, ditosylmethane, dimesylmethane and ditriflylmethane.

In some embodiments, an alkylating agent can be synthesized by halogenating the precursor thereof. In some embodiments, a halogen may be a radioisotope (e.g., $^{18}F, ^{123}I, ^{124}I, ^{125}I, ^{131}I, ^{76}Br$) and, therefore, also can be a label. In a preferred embodiment, a halogen can be $^{18}F$. In some embodiments, $^{18}F$ can be [$^{18}F$]fluoride and can be produced by any number of methods as known in the art. In some embodiments, $^{18}F$ can be produced by irradiating [$^{18}O$]$H_2O$ with high energy protons in a cyclotron to produce [$^{18}F$]HF/[$^{18}O$]$H_2O$, as known in the art 400. In some embodiments, [$^{18}F$] fluoride can be purified by chromatography, including but not limited to, ion-exchange chromatography 410 and other methods, as known in the art.

Methods of producing other radioisotopes are known in the art (see, e.g., *Handbook of Radiopharmaceuticcals* (Welch and Radvanly, eds., John Wiley & Sons, ©2003) and *Chemists' Views of Imaging Centers* 291-295 (Emran, ed., Penum Press 1995)). For example, methods of producing iodoradionuclides can be found in Finn, *Chemistry Applied to Iodine Radionuclides, in Handbook of Radiopharmaceuticals* 423-400 (Welch and Redvanly, eds., John Wiley & Sons, ©2003), and Washburn, et al., *Production and Application of $^{123}I$-Labeled M-Iodobenzylguanidine ($^{123}I$-MIBG) in Chemists' Views of Imaging Centers* 291-295 (Emran, ed., Penum Press 1995). Methods of producing bromoradionuclides can be found in Rowland, et al., *Radiobromine for Imaging and Therapy* 441-465 in *Handbook of Radiopharmaceuticcals* 423-400 (Welch and Radvanly, eds., John Wiley & Sons, ©2003).

In some embodiments, halogenating a precursor can be as described by Block et al., 1987, *J. Label. Compds. Radiopharm.* 24:1029-41. However, in some embodiments, the temperature of the halogenation reaction can be important in determining the yield of the alkylating agent. Therefore, in various exemplary embodiments the temperature of a halogenation reaction can be from about 40° C. to less than 80° C., from about 40° C. to about 50° C., from about 45° C. to about 50° C., or from about 20° C. to about 50° C. Generally, without being bound by theory, when halogenating an alkylating agent precursor, the alkylating agent that is synthesized can be more reactive with the halogen than the precursor which results in the synthesis of byproducts, including but not limited to dihaloalkanes. Therefore, lower temperatures (e.g., less than about 50° C.) can decrease the synthesis of byproducts. The skilled artisan will appreciate that lower temperatures decrease the rate of the halogenation reaction. Therefore, in some embodiments wherein the halogen is a radioisotope, the temperature and rate of the reaction can be adjusted to minimize the extent of radioisotope decay during the reaction. Determining the range of optimum temperatures and rates of the halogenation reaction is within the abilities of the skilled the artisan. However, in some embodiments reaction temperatures less than about 40° C. may be unsuitable when the radioactive isotope has a half-life that is less than about 2 hours. In some embodiments, halogenation can occur in the presence of a catalyst, including but not limited to a Kryptoflix® (e.g., Kryptoflix® 2.2.2) or a basic tetralkylammonium salt (e.g., tetrabutylammonium bicarbonate) 410. In some embodiments, potassium carbonate can provide a counter-ion for a halide ion, e.g., [$^{18}F$]fluoride. However, selecting the source and type of a counter-ion is within the abilities of the skilled artisan and can be influenced by the type of halide ion and/or target compound selected at the discretion of the practitioner. In some embodiments, the halogenation reaction can be agitated by any means, including but not limited to shaking, mixing and bubbling a substantially inert gas into the reaction (e.g., Argon, Nitrogen, Helium and the like) 450. In some embodiments, the agitation can be maintained as long as possible throughout the reaction.

In various exemplary embodiments, solid supports or resins can be used to minimize or inhibit the synthesis of dihaloalkyl byproducts. In some embodiments, the solid support or resin binds to a halide ion which can be used to halogenate a precursor. In some embodiments, the alkylating agent precursor can be a disulfonate ester, as described above. In some embodiments, a resin can be a polymer resin, e.g., polystyrene, containing a covalently attached quaternary ammonium salt (e.g., quaternary 4-dialkylaminopyridinium salts) (FIG. 12). In some embodiments a solid support can be QMA.

In some embodiments, the purified halide ions, e.g., [$^{18}F$] fluoride, can be dried using methods as known in the art, including but not limited to azeotropic drying under an Argon stream at a temperature from at least about 110° C. to at least about 115° C. 420 and cooled 430. In some embodiments, the azeotropic drying temperature may be higher or lower than this range, however, the skilled artisan will appreciate the affect of drying on the suitability of the halide ion for the synthesis of the alkylating agent and downstream uses of the alkylating agent rather than the actual temperature at which drying occurs.

Once made, an alkylating agent, in alternative embodiments, may be used with or without purification to alkylate or label a target compound 460. By "purification," "purify," and grammatical equivalents herein are meant to decrease the amount of extraneous matter, e.g., a byproduct, from a substance of interest. Therefore, in some embodiments an alkylating agent, once made, can be used directly to alkylate or label a target compound. In some embodiments, the target compound can be added directly to the vessel used to synthesize the alkylating agent. Therefore, in some embodiments an alkylating agent and an alkylated target compound can be produced in coupled reaction which in some embodiments may be a "one-pot, two-step" procedure.

In some embodiments, the amount of the target compound can be liquid at the start of the alkylation reaction and can be from about 0.2 mL to about 0.5 mL. In some embodiments, the target compound can be used neat. In some embodiments, the target compound can be diluted or dissolved in a solvent including but not limited to acetonitrile, dimethylsulfoxide (DMSO), dimethylformamide (DMF) and tetrahydrofuran (THF). Selecting the type of solvent for use with a target compound is within the abilities of the skilled artisan. In various exemplary embodiments, the alkylation of the target compound can occur at about 100° C., about 100° C. to about 130° C., or about 100 to about 110° C., or about 100 to about 105° C., for about 10 min. to about 25 min. and can be agitated as described above 460. Selecting a temperature and reaction period is within the abilities of the skilled artisan.

In some embodiments, a target compound is alkylated according to Scheme 1:

Scheme 1

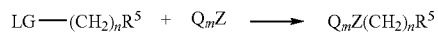

wherein,
n is an integer from 1 to 3;
$R^5$ is H or a label (X);
LG is a leaving group;
$Q_mZ$ is an alkylation reactive center of a target compound, wherein, m is an integer from 1-4 and each Q is independently H, alkyl, substituted alkyl, cycloalky, aryl and substituted aryl group, and wherein Z is N, O, S, P or C.
In some embodiments,
n is an integer from 1 to 2;
$R^5$ is a label (X);
LG is a sulfonate ester;
$Q_mZ$ is an alkylation reactive center of a target compound, wherein, m is an integer from 1-4 and each Q is independently H, alkyl, substituted alkyl, cycloalkyl, aryl and substituted aryl, and wherein Z is N, O, S, P or C.
In some embodiments,
n is an integer from 1 to 2;
X is a radiolabel;
LG is a mesylate, tosylate or triflate;
$Q_mZ$ is an alkylation reactive center of a target compound, wherein, m is an integer from 1-3 and each $Q_{1-3}$ is independently methyl and hydroxyethyl, and wherein Z is N.

Once the target compound is alkylated or labeled, in some embodiments, it can be purified by various means, as known in the art. For example, an alkylated target compound can be purified by electrophoresis, precipitation, extraction, and/or column chromatography 470 (e.g., ion exchange chromatography, molecular exclusion chromatography). Determining any one or more purification steps or methods for purifying an alkylated or labeled target compound is within the abilities of the skilled artisan. Thus, a skilled artisan will appreciate that purification of an alkylated or labeled target compound by for example chromatography can comprise one or more washing steps 480, 490 prior to elution 500. In some embodiments, the pH or ionic strength an alkylated or labeled target compound can be subsequently altered 510, 510. In some embodiments, an alkylated or labeled target compound can be purified so that it is suitable for use in a living subject 520.

Figure 4:
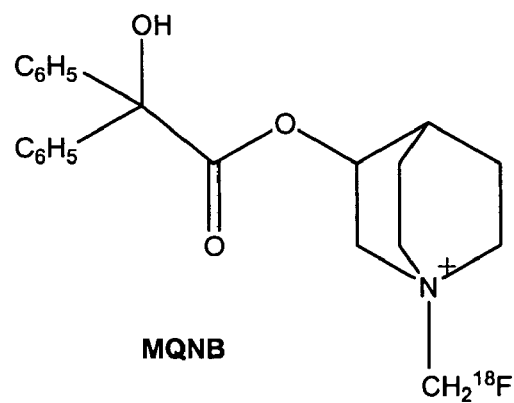
FIG. 4 depicts the structure of an [$^{18}$F]fluoroalkylated quaternary amine, 3-quinuclidinyl benzilate (MQNB), according to one embodiment.
Figure 6:
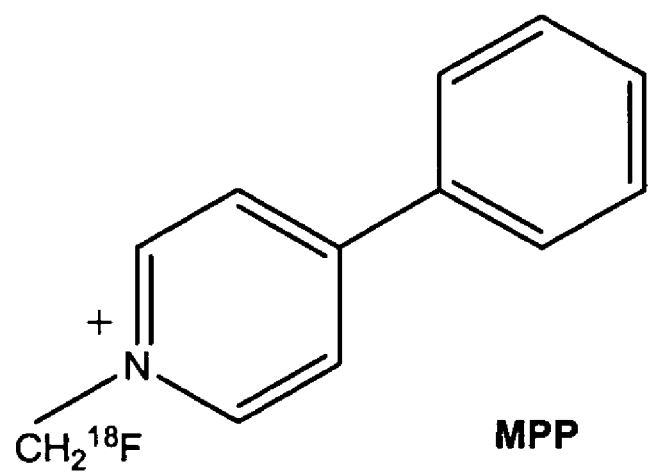
FIG. 6 depicts the structure of an [$^{18}$F]fluoroalkylated quaternary amine, N-methyl-4-phenyl-pyridinium (MPP), a neurotoxin, according to one embodiment.

By way of exemplification and not limitation, an alkylated target compound can be N-fluoromethyl-MQNB (FIG. 4), N-fluoromethyl-MPP (FIG. 6), N-fluoromethylspiperone (FNMS), [$^{18}$F]fluoromethyl-neostigmine, [$^{18}$F]fluoromethyl-tyrosine and 3-(2'-fluoroethyl)spiperone (FESP). In some embodiments, an alkylated target compound also can be labeled. Therefore, the present disclosure, in some embodiments, contemplates the radiolabeled target compounds.

Thus, in various exemplary embodiments the fluorine in each of the above can be substitute by $^{18}$F, $^{123}$I, $^{124}$I, $^{125}$I, $^{131}$I, or $^{76}$Br.

In some embodiments, an alkylated target compound can have a structure of Formula III:

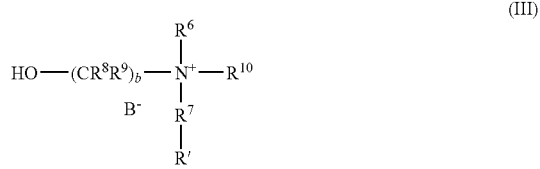

wherein,
R' is $^{18}$F, $^{123}$I, $^{124}$I, $^{125}$I, $^{131}$I or $^{76}$Br;
$B^-$ is a counterion;
b is an integer from 1 to 3;
$R^6$, $R^7$, $R^{10}$ are independently $CH_3$, $C_2H_5$, $C_3H_7$, $C_6H_5$;
$R^8$, $R^9$ are independently H, $CH_3$, $C_2H_5$.

Therefore, in various exemplary embodiments an alkylated target compound can be a choline analog (e.g., N,N-dimethyl-N-fluoromethylethanolamine (fluorocholine: FCH), N,N-dimethyl-N-fluoroethylethanolamine (fluoroethylcholine: FECh), [$^{18}$F]FCH, and [$^{18}$F]FECh, N,N-dimethyl-N-bromomethylethanolamine (bromocholine: BRCH), N,N-dimethyl-N-bromoethylethanolamine (bromoethylcholine: BrECh), [$^{76}$Br]BrCH, and [$^{76}$Br]BrECh, N,N-dimethyl-N-iodomethylethanolamine (iodocholine: ICH), N,N-dimethyl-N-iodoethylethanolamine (iodoethylcholine: IECh), [$^{125}$I]ICH, and [$^{125}$I]IECh, and the like.

In some alternative embodiments, an alkylated target compound can be other than [$^{18}$F]FCH, [$^{18}$F]FECh or [$^{18}$F]FDG (fluorodeoxyglucose), for example, wherein the alkylating agent used to prepare the alkylated compound is purified prior to an alkylation reaction.

In some embodiments, a process for making an [$^{18}$F]-labeled target compound ($T_c$) may comprise [$^{18}$F]fluoride and X—$(CH_2)_n$—X in a reaction vessel to form [$^{18}$F]-$(CH_2)_n$—X wherein X is tosylate, mesylate or triflate and n=1-4, adding a target compound comprising an alkylation reactive group to the reaction vessel to form [$^{18}$F]-$(CH_2)_n$-$T_c$ passing the reaction mixture through a first chromatographic support to bind the [$^{18}$F]-$(CH_2)_n$-$T_c$ and eluting the [$^{18}$F]-$(CH_2)_n$-$T_c$ from the support. In some embodiments, the reaction vessel can be in fluid communication with the first chromatographic support. In some embodiments, the first chromatographic support has an outlet which is in fluidic communication with a dispenser for delivering aliquots of eluent to the [$^{18}$F]-$(CH_2)_n$-$T_c$ to individual vials. In some embodiments, a second chromatographic support can be in fluid communication with and located between the first chromatographic support and the dispenser.

Once made, the alkylated or labeled target compounds (target compound derivative) may find use in vivo or in vitro at the discretion of the skilled artisan. In some embodiments, the alkylated or labeled target compound can be used to modify or label a second target compound. As exemplified in FIG. 13, a labeled amino acid can be attached to a peptide. In some embodiments, the method of attachment can employ solid-phase peptide synthesis processes as described for example in Bianco, et al., 2003, *Org. Biomol. Chem.* 1(23): 4141-3 (Epub 2003 Oct. 22); Deechongkit, et al., 2004, *Org Lett.* 6(4):497-500; Hojo, et al., 2004, *Chem. Pharm. Bull.* (Tokyo) 52(4):422-7; Malkinson, et al., *Org. Lett.* 5(26):50514; Merrifield, 1995, *Biopolymers* 37(1):34; Merrifield, 1997, *Methods Enzymol.* 289:3-13; Song, et al., 2004, *Bioorg. Med. Chem. Lett.* 14(1):161-5; Stephenson, et al., 2004, *Bioconjug. Chem.* 15(1):128-36; Wang, et al., 1987, *Int. J. Pept. Protein Res.* 30(5):662-667; and U.S. Pat. Nos. 4,507,230, 4,816,513, 5,186,898, 5,233,044, 5,258,454, 5,286,846, 5,380,495, 5,444,150.

In some embodiments, a labeled target compound may find use as a therapeutic, imaging agent, radiopharmaceutical, or tracer. Accordingly, in some embodiments, an alkylated or labeled target compound can be use to detect, monitor or analyze a cell or tissue in subject. In some embodiments, the cell or tissue may be benign, malignant, neoplastic and/or cancerous and can be staged by an imaging technique. In some embodiments, the imaging technique can be positron emission tomography (PET). Methods and techniques for performing PET are well-known in the art (see, e.g., U.S. Pat. Nos. 4,563,582, 4,642,464, 4,647,779, 4,677,299, 4,733,083, 4,864,138, 4,864,140, 5,027,817, 5,103,098, 5,138,165, 5,210,420, 5,224,037, 5,319,204, 5,378,893, 5,453,623, 5,591,977, 5,602,395, 5,744,802, 5,827,499, 5,998,792, 6,130,430, 6,288,399, 6,434,216, 6,521,893, 6,674,083, 6,718,006). Thus, in some embodiments an alkylated or labeled target compound can be formulated according to its intended use at the discretion of the practitioner. For use as an in vivo imaging agent, the labeled target compound is formulated to be suitable for intravenous injection (e.g., sterile, non-pyrogenic). In some embodiments, a labeled target compound can be formulated with a pharmaceutically acceptable carrier such as a pharmaceutically acceptable salt and a pharmaceutically effective amount is administered to a subject.

By "pharmaceutically acceptable salt" herein is meant a salt of a compound of the invention which is made with counterions which is understood in the art to be generally acceptable for pharmaceutical uses and which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfinuric acid, gluconic acid, glutamic acid, hydroxynaphthoic acid, salicylic acid, stearic acid, muconic acid and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine, morpholine, piperidine, dimethylamine, diethylamine and the like. Also included are salts of amino acids such as arginates and the like, and salts of organic acids like glucuronic or galacturonic acids and the like (see, e.g., Berge et al., 1977, J. Pharm. Sci. 66:1-19).

"Pharmaceutically effective amount" or "therapeutically effective amount" refers to an amount sufficient to produce the desired physiological effect or amount capable of achieving the desired result, particularly for diagnosing or treating disorders or disease conditions, including reducing or eliminating one or more symptoms of the disorder or disease or prevention of the disease or condition. Accordingly, in a preferred embodiment, a labeled target compounds can be administered in an mount sufficient to detect, monitor and/or stage a neoplasm in a subject. The amount administered and route of administration is selected at the discretion of the practitioner as known in the art.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesicaily or intrathecally. Parenteral administration, oral administration, subcutaneous administration and intravenous administration are the preferred methods of administration.

In various exemplary embodiments, the above methods of synthesizing an alkylating agent, the alkylation or labeling of a target compound, and/or the purification of the alkylated or labeled target compound can be automated. Thus, in some embodiments, the disclosed methods may be implemented on a general purpose or special purpose device, such as, a device having a processor for storing data and/or commands. It will be appreciated that the computing device may be a single computer or a plurality of networked computers and that the several procedures associated with implementing the methods and procedures described herein may be implemented on one or a plurality of computer devices. In some embodiments, the disclosed procedures and methods are implemented on standard server-client network infrastructures with various embodiments of the disclosed features added on top of such infrastructure or compatible herewith. Methods, processes and procedures described herein generally may be implemented in software, hardware and/or combinations thereof. In some embodiments, as exemplified in FIG. 10, processor 300 can be directed by readable memory 310. In some embodiments, processor 300 can be programmed to direct the purification of a halogen ion, e.g., [$^{18}$F]fluoride 100 using QMA 170. In some embodiments, processor 300 directs elution of [$^{18}$F]fluoride 100 from QMA 170 using K222/Carbonate 110 and directs the eluate to reaction vessel (RV) 210. In some embodiments, ditosylmethane 120 can be directed to reaction vessel 210. To synthesize an alkylating agent, e.g., [$^{18}$F]fluoromethane tosylate, processor 300 can direct temperature control module 320 to heat reaction vessel 210 to the programmed temperature selected at the discretion of the practitioner and can direct the mixing reactants, for example, by bubbling an inert gas, e.g., Argon 180. In some embodiments, processor 300 direct the addition of dimethylamine 130 to RV 210 which can be heated by thermal control module 320 and mixed by Argon 180 to synthesize an alkylated or labeled target compound, e.g., [$^{18}$F]FCH. EtOH/Water 140 can be directed to reaction vessel 320 by processor 300, which in some embodiments washes reaction vessel 320 and picks up additional alkylated product. In some embodiments, processor 300 directs the contents of reaction vessel 320 to silica column 200. Waste 230 does not bind to silica column 200 and, in some embodiments, alkylated product, e.g., [$^{18}$F] FCH can be eluted by AcOH 150. AcOH 150 can be removed by directing the eluate over weekly basic ion-exchange resin 240 and alkylated product, e.g., [$^{18}$F]FCH can be collected into vial 250. Valve 160 controls flow to and from QMA 170.

Three-way valves 190 and 220 control flow to and/or from silica column 200, waste 230, the weekly basic ion-exchange resin 240 and vial 250.

In some embodiments, the methods and procedures may be automated by the insertion of 3-way values 190 and 220, as shown, in a Siemens-CTI Chemical Process Control Unit (CPCU) (CTI, Inc., Knoxyille, Tenn.). As known in the art, CPCU has three components: a chemistry process control unit, a control chassis, an operating system and control software designed to be programmable by practitioners to direct a variety of procedures. As known in the art, a CPCU includes an IBM compatible PC system and a standard (STD) bus subsystem. The computer runs on Microsoft® Windows NT® Operating System and the Intellution® Software Package (see, e.g., [$^{18}F$]*Chemical Process Control Unit.* (CHF.SA 10.0796.0500, CTI, Inc., 1996); and Padgett et al., 1989, "Computer-controlled radiochemical synthesis: "A chemistry process unit for the automated production of radiopharmaceuticals." *Int. J. Rad. Appl. Instrum* [A]. 40(5):43345).

As used in this specification and the appended claims, the singular forms "a," "an" and "the" include plural unless the context clearly indicates otherwise. The following examples are offered by way of illustration or exemplification and not by way of limitation. Thus, it is understood that these examples in no way serve to limit the true scope of this disclosure. All references cited herein, including those patents and/or applications cited above Section 1. Cross-Reference to Related Application, are hereby incorporated by reference.

7. EXAMPLES

Reagents and solvents were obtained from Aldrich Chemical Co. and Fisher Scientific and used without further purification unless otherwise specified. Melting points were recorded on an Electrothermal 9100 (Electrothermal Engineering Ltd., Southend-on-Sea, UK) and are uncorrected. NMR spectroscopy was carried out on a Varian 400 MHz instrument (Varian Inc. Palo Alto, Calif.). Column chromatography was carried out 230 Mesh Silica Gel (Catalog No. 4791010, Whatman Inc., Clifton, N.J.). Thin layer chromatography (TLC) was performed on Silica 60 $F_{254}$ analytical plates (E. Merck, Catalog No. 4410222, Whatman Inc., Clifton, N.J.), equipped with a Bioscan 200 imaging scanner (Bioscan, Inc., Washington, D.C.). High pressure liquid chromatography (HPLC) was achieved on a Waters 600 System (Waters Corporation, Milford, Mass.) with a UV detector (see, e.g., FIGS. 15 and 17) (Catalog No. WAT080690, Waters Corporation, Milford, Mass.) and radioactivity detector (see, e.g., FIGS. 14 and 16) (Catalog No. FC3200, Bioscan, Inc., Washington, D.C.) attached in series, using a Partisil SCX column (250×4.6 mm, Catalog No. 8173, Alltech Associates, Deerfield, Ill.) eluted at 1 mL/min with a 20% acetonitrile/water solution containing 0.25 mol/L sodium dihydrogen phosphate. Gas chromatography (GC) was performed on a Hewlett-Packard 6890 GC (Hewlett-Packard Company, Palo Alto, Calif.) equipped with a CAM column (30 mm×0.25 µm, Catalog no. 1122132, J&W Scientific, Agilent Technologies, Inc., Palo Alto, Calif.).

Example 1

Ditosylmethane

Ditosylmethane was prepared by mixing diiodomethane (1.2 g, 4.5 mmol) and two fold of p-toluenesulfonate silver salt (2.8 g, 11 mmol) in anhydrous acetonitrile (20 mL). The resulting mixture was refluxed for 16 h. Ditosylmethane was purified using a 230 Mesh Silica Gel Column (Catalog No. 4791010, Whatman, Inc., Clifton, N.J.) (3040% ethylacetate-hexanes) to yield a white crystalline product (1 g, 63%): m.p. 117° C. (lit. m.p. 116-117° C.); $^1$H-NMR (CDCL$_3$, 400 MHz) δ 2.45 (s, 6H, CH$_3$), 5.10 (s, 2H, OCH$_2$O), 7.25 (d, J=8 Hz, 2H), 7.60 (d, J=8 Hz, 2H).

Example 2

N,N-Dimethyl-N fluoromethylethanolamine (Fluorocholine (FCH))

A sealed tube containing 10 mL anhydrous tetrahydrofuran (THF) and 2 mL (20 mmol) N,N-dimethylethanolamine was cooled at −78° C. Chlorofluoromethane (5.7 g, 70 mmol, Catalog No. 593-70-4, Synquest Labs, Alachua, Fla.) was bubbled through the cooled solution for 15 min. The mixture was allowed to slowly warm to room temperature overnight. A white solid formed, which was filtered, washed three times with cold (~5° C.) THF and dried under vacuum. FCH was isolated as a hygroscopic white solid (0.5 g, 15%): $^1$H-NMR (D$_2$O, 400 MHz) δ 3.24 (s, 3H, CH$_3$), 3.25 (s, 3H, CH$_3$), 3.60-3.63 (m, 2H, CH$_2$), 4.05-4.08 (m, 2H, CH$_2$OH), 5.43 (bd, J=45 Hz, 2H, CH$_2$F).

Example 3

[$^{18}$F]Fluoromethane tosylate and [$^{18}$F]fluoroethane-tosylate

No carrier added [$^{18}$F]fluorination of 1,1-1,2- and 1,3-disubstituted alkanes was systematically studied by Block et. al. (1987) *J. Label Compds. Radiopharm.* 24:1029-1042. We reproduced the results of Block, et al. in the [$^{18}$F]fluorination of ditosylmethane and 1,2-ditosylethane. Both reactions were heated at 80° C. for 5 min. and the products were analyzed by TLC. TLC was performed on Silica 60 F254 analytical plates (Catalog No. 4410222, Whatman Inc., Clifton, N.J.) in 30% Ethyl acetate/hexanes. [$^{19}$F]fluoride was included in these studies to provide a UV detectable moiety for quality control analysis.

Figure 1:
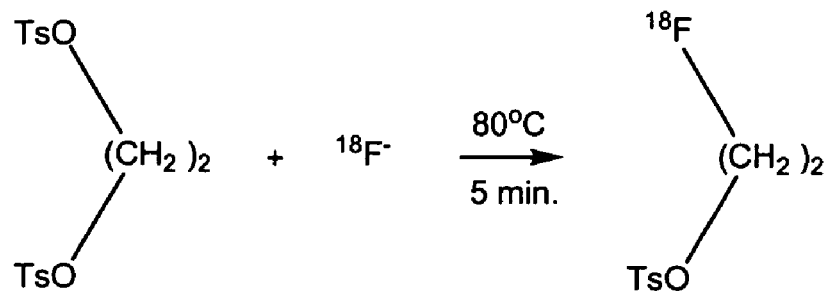
FIG. 1 depicts the synthesis of an alkylating agent, [$^{18}$F] fluoroethane tosylate, according to one embodiment.

[$^{18}$F]Fluorination of 1,2-ditosylethane resulted in an 80% yield of [$^{18}$F]fluoroethane tosylate (FIG. 1). [$^{18}$F][$^{19}$F]difluoroethane was not detected. Therefore, an electro withdrawing effect was not observed due to the [$^{18}$F]fluorine at the β position. The 80% yield was achieved without agitation of the reaction. [$^{18}$F]fluoroethane tosylate can be produced at lower temperatures but the skilled artisan will appreciate that as the temperature decreases the yield decreases.

Figure 2:
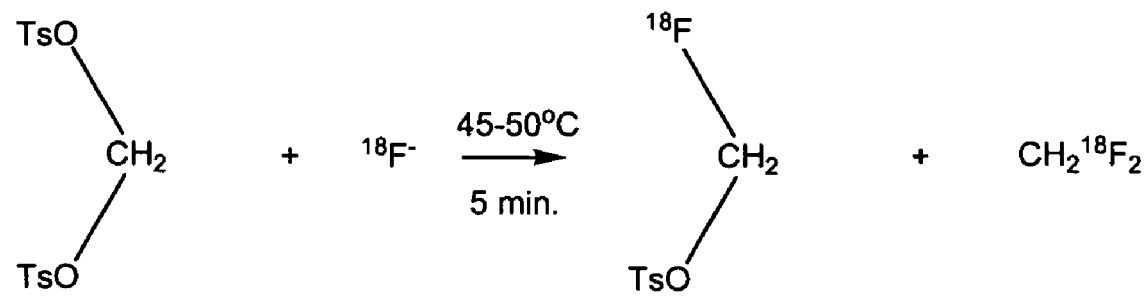
FIG. 2 depicts the synthesis of an alkylating agent, [$^{18}$F] fluoromethane tosylate, according to one embodiment.

[$^{18}$F]fluorination of ditosylmethane yielded two labeled products, [$^{18}$F]difluoromethane and [$^{18}$F][$^{19}$F]difluoromethane tosylate, under various conditions. At 80° C., only one product is formed, the byproduct [$^{18}$F][$^{19}$F]difluoromethane which is not useful for the synthesis of [$^{18}$F]fluorocholine. In addition, some free, detectable [$^{18}$F]fluoride is not uncommon, especially when the reaction is not pushed to completion. As expected by the studies of Block et al., the yield of [$^{18}$F]fluoromethane tosylate was ~1% (FIG. 2). The low yield of [$^{18}$F]fluoromethane tosylate may be the result of [$^{18}$F]fluoromethane tosylate being more reactive than ditosylmethane in SN$_2$ reactions due to the electrowithdrawing effect of the fluorine at the α position. Due to the very low concentration of [$^{18}$F]fluoride detected after the reaction, apparently [$^{18}$F]fluoromethane tosylate may undergo a second fluorination with [$^{19}$F] carrier present in the reaction vessel to produce [$^{18}$F][$^{19}$F]difluoromethane, a very volatile compound (boiling point=−52° C.).

We examined the affects of temperature on the fluorination of ditosylmethane. When the reaction temperature was lowered to about 45-50° C., the production of [$^{18}$F][$^{19}$F]difluoromethane decreased and we obtained sufficient amounts of [$^{18}$F]fluoromethane tosylate to synthesize [$^{18}$F]FCH (FIG. 2). At temperatures less than about 40° C. for up to 20 min., only a small amount of [$^{18}$F][$^{19}$F]difluoromethane was detected; however, the reaction rate may be unsuitable for radio-synthesis using some short-lived isotopes. At temperatures greater than about 50° C., the major reaction product was [$^{18}$F][$^{19}$F]difluoromethane.

The fluorination step also was sensitive to agitation. At temperatures ranging from about 40° C. to about 50° C., in the absence of agitation, the reaction yielded low amounts of [$^{18}$F][$^{19}$F]difluoromethane but also yield low amounts of [$^{18}$F]fluoromethane tosylate (~10% yield). Performing the [$^{18}$F]fluorination at temperatures ranging from about 40° C. to about 50° C. with agitation, produced sufficient quantities of [$^{18}$F]fluoromethane tosylate (~30% yield) to synthesize [$^{18}$F]FCH.

Example 4

[$^{18}$F]N,N-Dimethyl-N-fluoromethylethanolamine ([$^{18}$F]FCH)

[$^{18}$F]FCH was prepared in a 2-step reaction: fluorination of ditosylmethane with [$^{18}$F]fluoride followed by an alkylation reaction with [$^{18}$F]fluoromethane tosylate and dimethylethanolamine using a modified Siemens-CTI Chemical Process Control Unit (CPCU, Catalog No. 3601037, CTI, Knoxyille, Tenn.) (FIG. 10). [$^{18}$F]FCH was purified using a Silica Sep-Pak column (Catalog No. WAT023537, Waters Corporation, Milford, Mass.). The column was washed with ethanol and water to remove all impurities and [$^{18}$F]FCH was eluted with 2% acetic acid. The acetic acid was removed using an AG 4-X4 weakly basic ion-exchange resin column (143-3341, Bio-kad Laboratories, Inc., Hercules, Calif.) (see AG 4 Instruction Manual LIT207 Rev B, Bio-Rad). Two 3-way slider valves, e.g., teflon slider valves, were added to the CPCU to perform the purification (FIG. 10). The software was modified to lower the temperature and to permit agitation for the labeling step.

Figure 3:
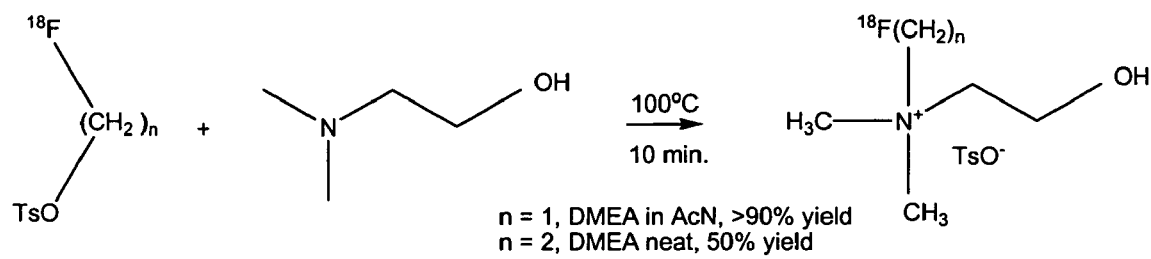
FIG. 3 depicts the [$^{18}$F]fluoroalkylation of dimethylethanolamine, according to one embodiment.

To prepare [$^{18}$F]fluoride, enriched $^{18}$O-water was irradiated with an 11 MeV proton (33 μA for 60 min.). After bombardment, the target $^{18}$F—HF/$^{18}$O-water solution was transferred to an anion-exchange QMA cartridge (carbonate form) (Catalog No. WAT054725, Waters Corporation, Milford, Mass.) using Ar pressure. The no-carrier-added [$^{18}$F]fluoride was trapped on the QMA cartridge and $^{18}$O-water was recovered. The [$^{18}$F]fluoride was eluted from the cartridge with 1 mL acetonitrile:water solution (19:1) containing 2.2 mM potassium carbonate ($K_2CO_3$) and 40 mM Kryptofix® 2.2.2 (4,7,13,16,21,24-hexaoxa-1,10-diazabicyclo[8.8.8]hexacosane, $C_{18}H_{36}N_2O_6$, Catalog No. 291110, Sigma-Aldrich Corp, St. Louis, Mo.) into the reaction vessel. The mixture was azeotropically dried under an Ar stream at 110° C. for 4 min. and allowed to cool for about 60 sec. Ditosylmethane (10 mg, 0.03 mM) in 1 ml anhydrous acetonitrile was added to the dry residue. The mixture was heated at 45-50° C. for 5 min. with intermittent Ar gas bubbling (10 sec. for every 20 sec.). Afterwards, 1 mL acetonitrile containing 0.2 mL of N,N-dimethylethanolamine was added to the reaction vessel, which was heated at 100° C. for 10 min. with intermittent Ar gas bubbling (15 sec. for every 30 sec.) (FIG. 3). The entire mixture was loaded onto a $SiO_2$ Sep-Pak cartridge (Catalog No. WAT023537, Waters Corporation, Milford, Mass.) and washed with ethanol (3×5 mL) and water (2×5 mL). The flow was redirected to the final product vial using two 3-way valves. [$^{18}$F]FCH was released from the $SiO_2$ Sep-Pak cartridge with 5 mL 2% acetic acid followed by 5 ml $H_2O$. Acetic acid was stripped out of the eluant by an AG 4-X4 weakly basic ion-exchange resin column (Catalog No. 143-3341, Bio-Rad Laboratories, Inc., Hercules, Calif.) (see AG 4 Instruction Manual LIT 207 Rev B, Bio-Rad) and the solution was passed through a 0.2 μm membrane filter (Catalog No. SLGS V255F, Millipore Corp, Billerica, Mass.) into a sterile vial containing 0.5 ml 23.4% sodium chloride concentrated solution. Alternatively, the $SiO_2$ Sep-Pak cartridge was replaced by a pre-activated (10 mL 1 N HCl) Accell cartridge (Catalog No. WAT023531, Waters Corp, Millford, Mass.) and [$^{18}$F]FCH was eluted with 10 mL saline.

The results of the alkylation reaction indicated that [$^{18}$F]fluoromethane tosylate reacted almost quantitatively with N,N-dimethylethanolamine in acetonitrile to provide a >90% yield of [$^{18}$F]FCH. The overall yield of the synthesis of the [$^{18}$F]fluoromethane tosylate to [$^{18}$F]FCH was 20%, which may be due to the production of [$^{18}$F][$^{19}$F]difluoromethane during the fluorination step. The total synthesis time was less than about 40 min. (see FIGS. 16 and 17).

Example 5

N,N-Dimethyl-N-fluoroethylethanolamine (fluoroethylcholine(FECh)) Synthesis

1-Bromo-2-fluoroethane (1 g, 8 mmol) was dissolved in N,N-dimethylethanolamine (0.7 g, 8 mmol) and heated at 100° C. for 10 min. The resulting mixture was taken up in 10% ethanol/ethylacetate. After removal of the solvent, FECh was obtained as a white solid (1.7 g, 100%). $^1$H-NMR spectrum was indistinguishable from the spectrum reported by Hara, et. al., 2002, *J. Nucl. Med.* 43(2):187-199.

Example 6

[$^{18}$F]N,N-Dimethyl-N-fluoroethylethanolamine ([$^{18}$F]FECh) Synthesis

Anhydrous [$^{18}$F]flouride was obtained as described in Example 3 and reacted with 1,2-bis-ditosylethane (10 mg, 0.03 mmol) in 1 mL anhydrous acetonitrile. The mixture was heated at 80° C. for 5 min with intermittent Ar gas bubbling (10 sec for every 20 sec). Afterward, 0.3 mL N,N-dimethylethanolamine neat was added to the reaction vessel, which was heated at 100° C. for 10 min. with intermittent Ar gas bubbling (15 sec for every 30 sec). [$^{18}$F]FECh was purified from the reaction mixture as described in Example 3 using a Silica Gel Sep-Pak cartridge.

Alkylation with [$^{18}$F]fluoroethane tosylate in N,N-dimethylethanolamine neat gave only a 50% yield. The overall yield of [$^{18}$F]FECh also was 50%, which is higher than the yield of [$^{18}$F]FCH (20%). This may be a result of very little to no [$^{18}$F][$^{19}$F]difluoroethane byproduct being produced during the fluorination step. As described above for [$^{18}$F]FCH, the total synthesis time was less than about 40 min. (see FIGS. 14 and 15).

Example 7

[$^{18}$F]FCH and [$^{18}$F]FECh Purification

[$^{18}$F]FCH and [$^{18}$F]FECh are quaternized alkylamines, which can be absorbed strongly onto Silica Gel Sep-Pak cartridges (Mulholland, et. al. (1999) *J. Label Compounds Radiopharm.* 42:Suppl. 1 s459-s461). [$^{18}$F]FCH and [$^{18}$F]FECh tightly held onto the cartridges which allowed most impurities to be quickly removed to waste with an ethanol elution. [$^{18}$F]FCH and [$^{18}$F]FECh were eluted with a 2% acetic acid solution and neutralized using a weakly basic ion-exchange resin (AG 4-X4, Catalog No. 140-4341, Bio-Rad Laboraotires, Inc., Hercules, Calif.).

The radiochemical purity of [$^{18}$F]FCH and [$^{18}$F]FECh were determined by HPLC (HPLC 600 System, Waters Corporation, Milford, Mass.) and TLC (Silica 60 F254 Analytical Plates, Whatman Inc., Clifton, N.J.). [$^{18}$F]FCH and [$^{18}$F]FECh eluted from the HPLC column at 6.8 and 7.5 min, respectively. HPLC was achieved on a Waters 600 System (Waters Corporation, Milford, Mass.) with a UV detector (Catalog No. WAT080690, Waters Corporation, Milford, Mass.) and radioactivity detector (Catalog No. FC3200, Bioscan, Inc., Washington, D.C.) attached in series, using a Partisil SCX column (250×4.6 mm, Catalog No. 8173, Alltech Associates, Deerfield, Ill.) eluted at 1 mL/min with a 20% acetonitrile/water solution containing 0.25 mol/L sodium dihydrogen phosphate. The residual amounts of N,N-dimethylethanolamine in the final solutions were analyzed by GC using a CAM Column designed for amines (Catalog No. 1122132, Agilent Technologies, Inc., Palo Alto, Calif.). The only chemical contaminants detected by HPLC and GC were N,N-dimethylethanolamine (<0.5 mg per batch) and ethanol (<5 mg per batch).

To lower the N,N-dimethylethanolamine contamination, Silica Gel Sep-Pak cartridges were replaced with an Accell cartridge (Hara, et. al. (1997) *J. Nucl. Med.* 38(6):842-847). The Accell cartridge was preconditioned with HCl and H$_2$O and the final products were eluted with saline solution. N,N-Dimethylethanolamine was found to be <0.1 mg per batch in the [$^{18}$F]FCH preparation. [$^{18}$F]FECh was not efficiently purified using the Accell cartridge, i.e., about half of the [$^{18}$F]FECh was found in the waste fraction.

The final purified solutions in physiologic saline [$^{18}$F]FCH and [$^{18}$F]FECh were cultured (1 mL) for microorganisms for growth in enriched thioglycollate at 37° C. and trypticase soy broth media at 23° C. No growth was observed for 2 weeks. The final purified solutions were shown to be pyrogen free using the standard methodology for the LAL (Charles River Labs Endosafe, Charleston, S.C.). A positive control standard is always included in the assay. [$^{18}$F]FCH is currently in an FDA approved pre-clinical IND safety trial in humans. To date, after about fifty trials, no adverse effects from any [$^{18}$F]fluorocholine tested has been observed.

TLC plates were pre-treated in 2% acetic acid and air dried before use. The plates were eluted in 2% acetic acid. The R$_f$ [$^{18}$F]FCH and [$^{18}$F]FECh was 0.40, which confirms the HPLC results.

Example 8

Other Alkylating Agents, Alkylation Methods and Purification Methods

Alkylating Agents:

Alternatives to the tosylate leaving group for the SN$_2$ nucleophilic substitution reaction used for preparing [$^{18}$F]FCH and [$^{18}$F]FECh include but are not limited to halides and other sulfonate esters, such as, methane sulfonates (e.g., mesylates) and trifluoromethane sulfonates (e.g., triflates). However, as the volatility of an alkylating agent increases maintaining the alkylating agent in solution decreases. Therefore, by increasing the number carbon atoms the volatility can be decreases such that the alkylating agent can be maintained in solution.

Labeling 1,2-ditritylethane with [$^{18}$F]fluoride provides >80% yield of [$^{18}$F]fluoroethane triflate. This is greater than the yield of [$^{18}$F]fluoroethane tosylate because triflate is the most reactive of the three sulfonate esters (mesylate, tosylate, triflate). Moreover, a higher yield is achieved at the alkylation step with N,N-dimethylethanolamine using triflate as the leaving group. Alkylation using 2-[$^{18}$F]fluoroethane tosylate and N,N-dimethylethanolamine provides a 50% yield of [$^{18}$F]FECh. In contrast, 2-[$^{18}$F]fluoroethane triflate reacts with N,N-dimethylethanolamine to yield [$^{18}$F]FECh quantitatively. Thus the overall yield of [$^{18}$F]FECh using 1,2-ditritylethane as the unlabeled precursor is >70%.

As a result of our studies of the labeling ditosylmethane with [$^{18}$F]fluoride, the second fluorination is activated by the electrowithdrawing effect of the [$^{18}$F]fluorine in the α position leading to the synthesis of difluoromethane. Therefore, step(s) to slow or prevent the second activated fluorination are beneficial. Polymer resin supports containing covalently bound quaternary ammonium salts (see, e.g., *J. Labelled. Cpd. Radiopharmceuticals* 26:378-380 (1989), FIG. 12) or solid support such as QMA retain no-carrier-added [$^{18}$F]fluoride from irradiated [$^{18}$O]H$_2$O and label ditosylmethane. Polymeric resin processes may not be as efficient as solution reactions but they do slow or prevent the formation of [$^{18}$F][$^{19}$F]difluoromethane.

Alkylation:

Because sulfonate esters are more reactive than halide esters, [$^{18}$F]fluoromethane tosylate and [$^{18}$F]fluoroethane tosylate are suitable for on-column alkylation with N,N-dimethylethanolamine. The sulfonate esters are trapped on a Sep-Pak C18 cartridge loaded with the dimethylethanolamine. The [$^{18}$F]fluoromethylation of N,N-dimethylethanolamine thus is streamlined and the alkylation step is faster.

Purification:

We have shown that purification of [$^{18}$F]FCH was performed either using Silica Gel or Accell cartridges. However, [$^{18}$F]FECh was efficiently purified on Silica Gel but not on an Accell cartridge. This may be due to the alkylation step conditions which require the use of N,N-dimethylethanolamine without dilution (neat). With [$^{18}$F]FCH, alkylation occurs in a solvent, acetonitrile. Therefore, before loading the [$^{18}$F]FECh reaction mixture onto the Accell cartridge 1 mL acetonitrile is added, which permits [$^{18}$F]FECh to hold on to the Accell cartridge to facilitate purification.

Example 9

Other [$^{18}$F]-Labeled Target Compounds

Figure 5:
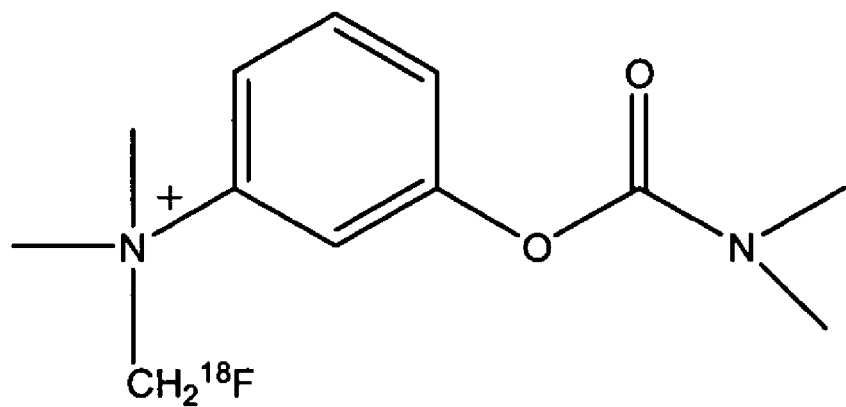
FIG. 5 depicts the structure of an [$^{18}$F]fluoroalkylated quaternary amine, neostigmine, an acetylcholinesterase inhibitor, according to one embodiment.
Figure 7:
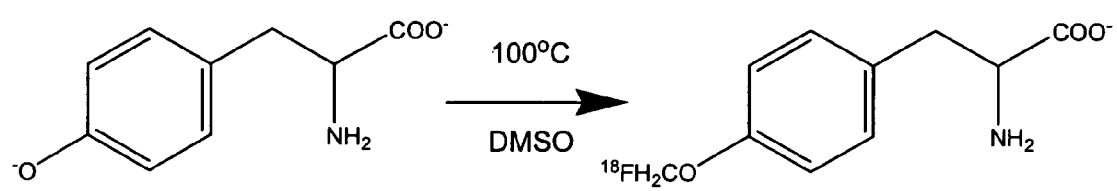
FIG. 7 depicts the O-fluoroalkylation of tyrosine (Tyr) using [$^{18}$F]fluoromethyl tosylate in dimethylsulfoxide (DMSO), according to one embodiment.
Figure 8:
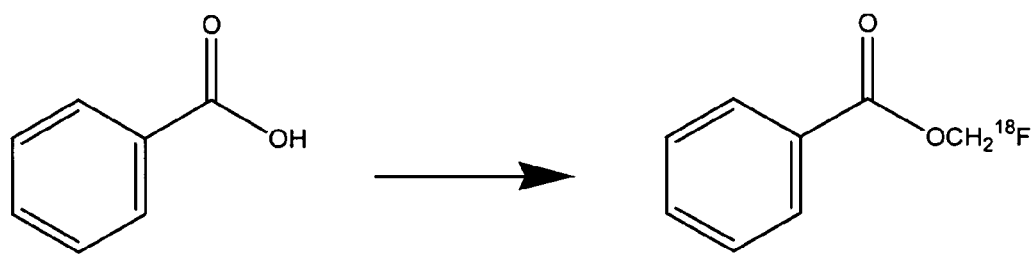
FIG. 8 depicts the O-fluoroalkylation of a carboxylic acid, benzoic acid, according to one embodiment.
Figure 9:
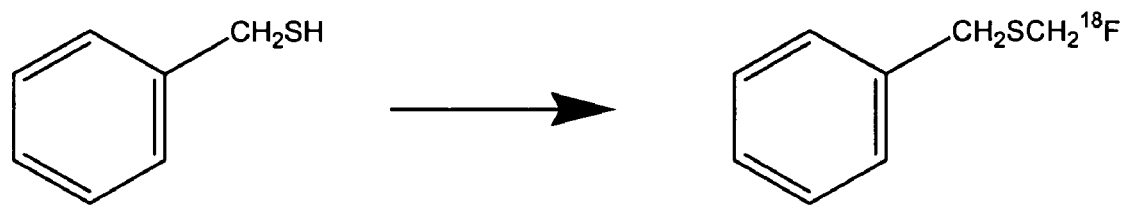
FIG. 9 depicts the S-fluoroalkylation of benzyl mercaptan (α-toluenethiol), according to one embodiment.

The disclosed methods can be used to replace target compounds labeled with [$^{11}$C]alkyl iodides with equivalent compounds labeled with longer-lived halogens, such as, $^{18}$F. Therefore, [$^{18}$F]fluoroalkane sulfonates can be used for various N, O, S and C alkylations. Examples of quaternary amines that may be [$^{18}$F]fluoroalkylated by the disclosed methods include MQNB (3-quinuclidinyl benzilate derivatives), a muscarinic ligand (FIG. 5); acetylcholinesterase inhibitor neostigmine (FIG. 6) and its metabolite TMA-phenyl; neurotoxin N-methyl-4-phenyl-pyridinium are labeled using this methodology. Secondary amines that can be [$^{18}$F]fluoromethylated according to the disclosed methods include [$^{18}$F]N-methylspiperone ([$^{18}$F]NMS) and 3-(2'-[$^{18}$F]fluoroethyl)spiperone ([$^{18}$F]FESP) (FIG. 7). O-alkylation reactions are used to methylate the amino acid tyrosine in the presence dimethylsulfoxide (DMSO) (FIG. 8). Carboxylic acids are alkylated as shown in FIG. 9). S-alkylation reactions are used to fluoromethylate the target compound of FIG. 9.

What is claimed is:

1. A method of alkylating a target compound comprising:
   a) synthesizing an alkylating agent having the formula:

$$^{18}F—CH_2—LG$$

wherein,
   LG is a leaving group, and wherein said synthesizing occurs at a temperature from about 40° C. to about 50° C.; and
   b) reacting said alkylating agent with a target compound comprising an alkylation reactive group under conditions suitable for the alkylation of said target compound, wherein said reacting is accomplished without purifying said alkylating agent after said synthesizing.

2. The method according to claim 1, wherein said LG is a sulfonate ester.

3. The method according to claim 1, wherein the precursor of said alkylating agent has the formula LG-CH$_2$-LG.

4. The method according to claim 1, 2, or 3, wherein LG is selected from the group consisting of tosylate, mesylate or triflate ester.

5. The method according to claim 1, wherein said alkylation reactive group comprises an alkyl, substituted alkyl, alcohol, carboxyl acid, saturated cycloalkyl, unsaturated cycloalkyl, aryl, substituted aryl, saturated heterocycle, unsaturated heterocycle, sulfhydryl, amine, N, O, S or C.

6. The method according to claim 1, wherein said target compound is selected from the group consisting of morphine, heroin, pethine, tamoxifen, codeine, nicotine, thioproperazine, diazepam, caffeine, flunitrazepam, hexamethonium, methiodide, quinuclidinyl benzilatem MQNB, neostigmine, MPP, NMS, tyrosine, spiperone, and spiroperidol.

7. The method according to claim 6, wherein said alkylated target compound is [$^{18}$F]fluoromethyl-MQNB, [$^{18}$F]N-fluoromethyl-MPP, [$^{18}$F]FNMS, [$^{18}$F]fluoroethylspiperone, [$^{18}$F]fluoromethyl-neostigmine, or [$^{18}$F]fluoromethyl-tyrosine.

8. The method according to claim 1, wherein said target compound is selected from the group consisting of glucose, lactic acid, hexobarbital, thymidine, iodoantipyrine, antipyrine and coenzyme Q.

9. The method according to claim 1, wherein said target compound is dimethylethanolamine.

10. The method according to claim 9, wherein the alkylated target compound is [$^{18}$F]N,N-dimethyl-N-fluoromethylethanolamine.

11. A method of synthesizing an $^{18}$F-labeled target compound comprising,
    a) synthesizing an alkylating agent having the formula:

$$^{18}F—CH_2—LG$$

wherein,
    LG is a leaving group, and wherein said synthesizing occurs at a temperature from about 40° C. to about 50° C.; and
    b) contacting said alkylating agent with a target compound comprising an alkylation reactive group under conditions suitable for the alkylation of said target compound, wherein the alkylated target compound is other than [$^{18}$F]FCH, [$^{18}$F]FECh or [$^{18}$F]fluorodeoxyglucose, and wherein said contacting is accomplished without purifying said alkylating agent, after said synthesizing.

12. The method according to claim of claim 11, wherein LG is a sulfonate ester.

13. The method according to claim 12, wherein said sulfonate ester is selected from the group consisting of tosylate, mesylate and triflate ester.

14. The method according to claim 11, wherein said target compound is selected from the group consisting of morphine, heroin, pethine, tamoxifen, codeine, nicotine, thioproperazine, diazepam, caffeine, flunitrazepam, hexamethonium, methiodide, quinuclidinyl benzilatem MQNB, neostigmine, MPP, NMS, tyrosine, spiperone, and spiroperidol.

15. The method according to claim 14, wherein said alkylated target compound is [$^{18}$F]fluoromethyl-MQNB, [$^{18}$F]N-fluoromethyl-MPP, [$^{18}$F]FNMS, [$^{18}$F]fluoroethylspiperone, [$^{18}$F]fluoromethyl-neostigmine, or [$^{18}$F]fluoromethyl-tyrosine.

16. The method according to claim 11, wherein said target compound is selected from the group consisting of glucose, lactic acid, hexobarbital, thymidine, iodoantipyrine, antipyrine and coenzyme Q.

17. A method of alkylating dimethylethanolamine comprising:
    a) synthesizing an alkylating agent having the formula:

$$^{18}F—CH_2—LG$$

wherein LG is a leaving group
    wherein said synthesizing occurs at a temperature from about 40° C. to about 50° C.; and
    b) reacting said alkylating agent with a dimethylethanolamine under conditions suitable for the alkylation of said dimethylethanolamine, wherein said reacting is accomplished without purifying said alkylating agent after said synthesizing.

18. The method according to claim 17, wherein LG is a sulfonate ester.

19. The method according to claim 17, wherein the precursor of said alkylating agent has the formula $$LG—CH_2—LG.$$

20. The method according to claim 17, 18 or 19, wherein LG is selected from the group consisting of tosylate, mesylate or triflate ester.

21. The method according to claim 17, wherein said fluoroalkylated choline is [$^{18}$F]N,N-dimethyl-N-fluoromethyl-ethanolamine.

22. A method according to claim 1, 11 or 17, wherein said synthesizing occurs at a temperature from about 45° C. to about 50° C.

23. A method according to claim 1, 11 or 17, wherein said synthesizing further comprises agitation.

* * * * *